US009528101B2

(12) United States Patent
Barth et al.

(10) Patent No.: US 9,528,101 B2
(45) Date of Patent: Dec. 27, 2016

(54) GRANZYME B PROTEASE VARIANTS

(71) Applicant: PHARMEDARTIS GMBH, Aachen (DE)

(72) Inventors: Stefan Barth, Aachen (DE); Sonja Schiffer, Jüchen (DE); Grit Hehmann-Titt, Aachen (DE)

(73) Assignee: PHARMED ARTIS GmbH, Aachen (DE)

( * ) Notice: Subject to any disclaimer, the term of this patent is extended or adjusted under 35 U.S.C. 154(b) by 11 days.

(21) Appl. No.: 14/346,600

(22) PCT Filed: Sep. 21, 2012

(86) PCT No.: PCT/EP2012/068607
§ 371 (c)(1),
(2) Date: Mar. 21, 2014

(87) PCT Pub. No.: WO2013/041659
PCT Pub. Date: Mar. 28, 2013

(65) Prior Publication Data

US 2014/0356347 A1 Dec. 4, 2014

Related U.S. Application Data

(60) Provisional application No. 61/538,368, filed on Sep. 23, 2011.

(30) Foreign Application Priority Data

Sep. 23, 2011 (EP) .................................... 11007764

(51) Int. Cl.
*C12N 9/48* (2006.01)
*C12N 9/64* (2006.01)
*A61K 47/48* (2006.01)

(52) U.S. Cl.
CPC ....... *C12N 9/6467* (2013.01); *A61K 47/48561* (2013.01); *C12N 9/6421* (2013.01)

(58) Field of Classification Search
None
See application file for complete search history.

(56) References Cited

FOREIGN PATENT DOCUMENTS

| | | | |
|---|---|---|---|
| WO | 2004031733 | A2 | 4/2004 |
| WO | 2005100556 | A2 | 10/2005 |
| WO | 2006026451 | A2 | 3/2006 |

OTHER PUBLICATIONS

NCBI Acc#ACD40304 from Rollman et al, 2008. Alignment with SEQ ID No. 1.*
UniParc Accession No. G1S047.1, Jun. 21, 2011. Alignment with residues 28-202 of SEQ ID No. 1.*
UniProtKB Accession No. B8XTR7, Mar. 3, 2009. Alignment with residues 28-202 of SEQ ID No. 1.*
ISR plus EPO written opinion for PCT/EP2012/068607.
Nucleotide Sequence XP002688092.
Ruggles SW et al. "Characterization of Structural Determinants of Granzyme B Reveals Potent Mediators of Extended Substrate Specificity," Journal of Biological Chemistry vol. 279, No. 29, Jul. 16, 2004, pp. 30751-30759.
Rosenblum MG et al. "Development of Novel, Highly Cytotoxic Fusion Constructs Containing Granzyme B: Unique Mechanisms and Functions," Current Pharmaceutical Design, 2009, vol. 15, No. 23, Aug. 1, 2009, pp. 2676-2692.

* cited by examiner

*Primary Examiner* — Sheridan Swope
(74) *Attorney, Agent, or Firm* — Wagenknecht IP Law Group PC

(57) ABSTRACT

The present disclosure provides novel variants of enzymes exhibiting serine protease activity; nucleic acid molecules encoding said proteases, vectors, host cells containing the nucleic acids and methods for preparation and producing such enzymes; compositions and complexes comprising at least one of the proteases; and methods for using such enzymes as a part of an immunoprotease, in particular for the treatment of cancer.

12 Claims, 18 Drawing Sheets

FIGURE 1
Examples for two used fusion proteins including granzyme B variants
A)
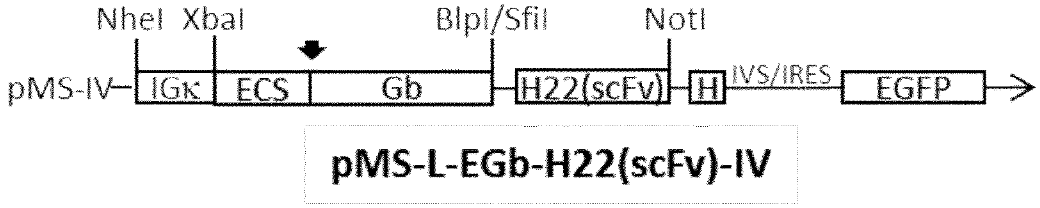
B)
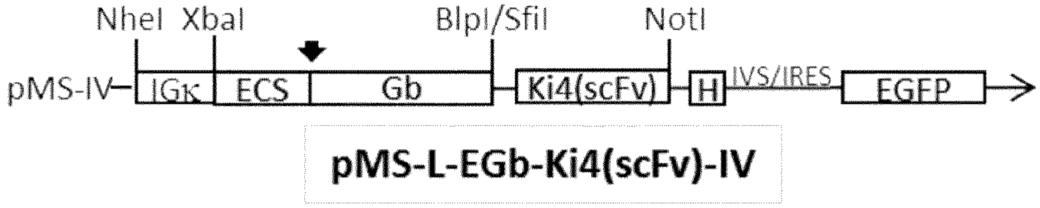

Expression of Granzyme B mutants

(A) (B)

Determination of endogenous Serpin B9 in different cell lines via flow cytometry

Determination of Serpin B9 in different cell lines via Western blot analysis

Specific binding of Gb-Ki4(scFv) mutants to target cells

FIGURE 7
Apoptosis assay of Gb-Ki4(scFv) mutants on target cells: flow cytometry (Dot plots)
(A)
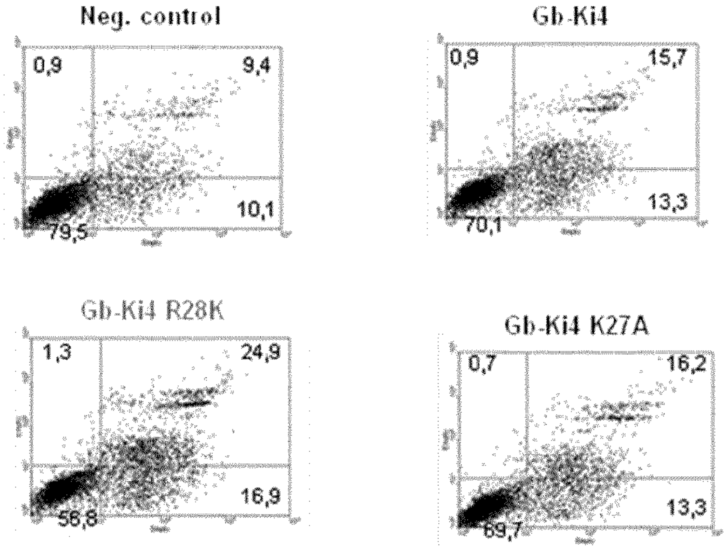
(B)
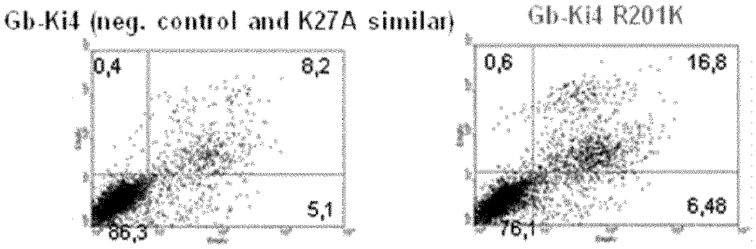

FIGURE 8
Apoptosis assay of Gb-Ki4(scFv) mutants on PI9$^+$ L1236 target cells
(A)
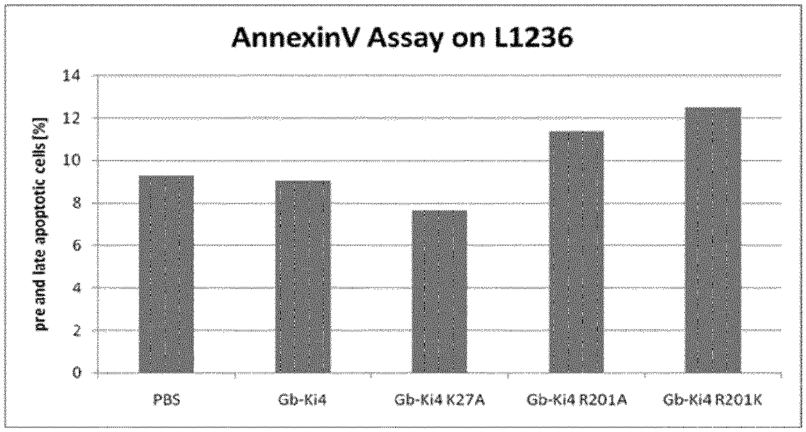
(B)
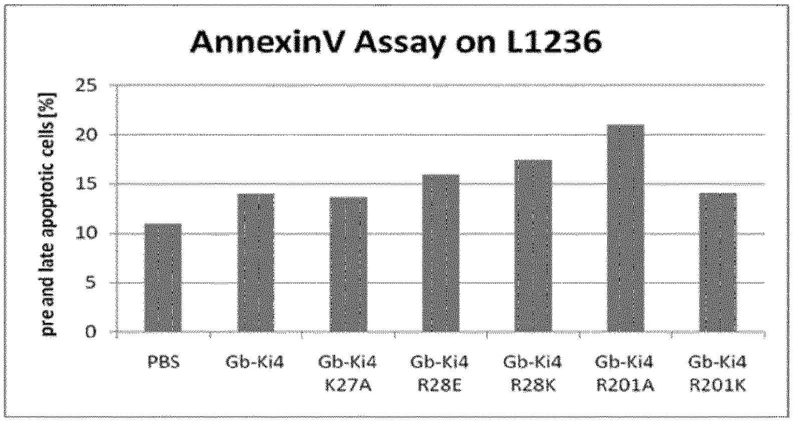
(C)
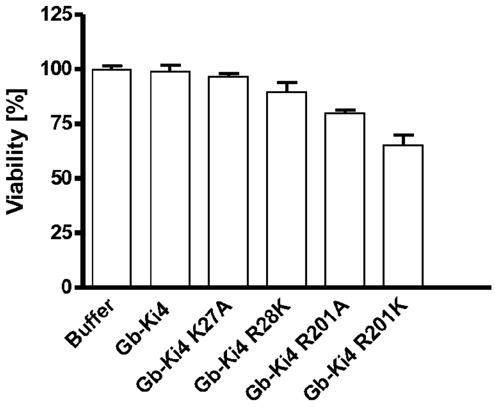

FIGURE 9
Apoptosis assay of Gb-Ki4(scFv) mutants on PI9$^{+}$ L428 target cell line
(A)
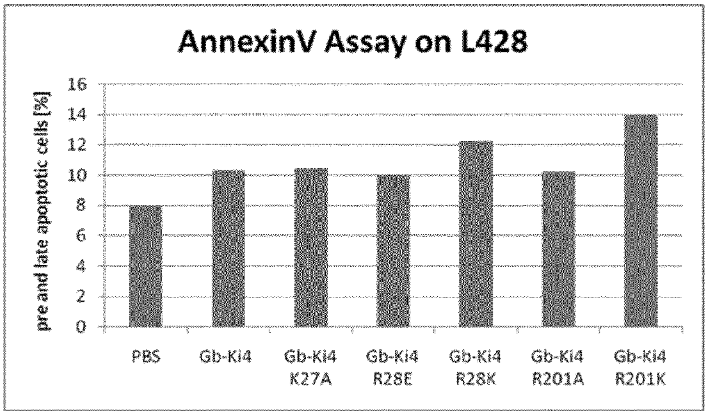
(B)
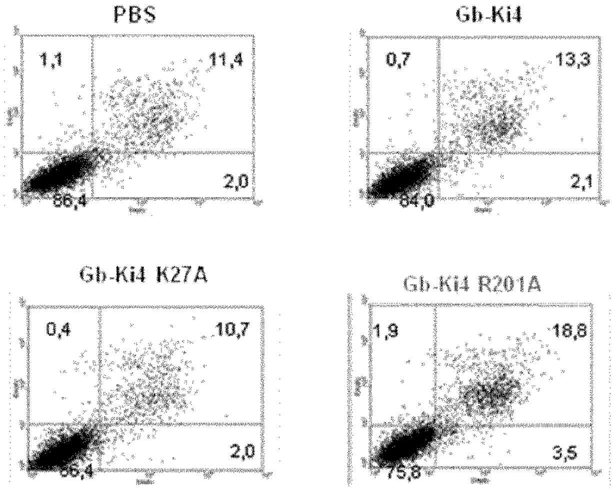
(C)
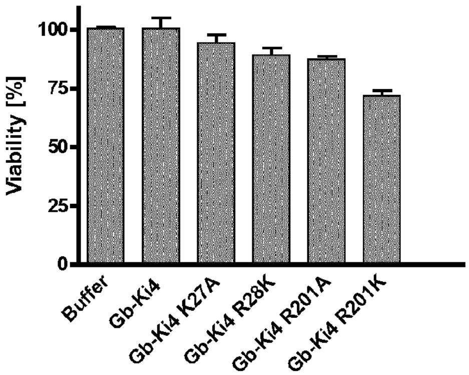

FIGURE 10

A) Amino acid sequence of human wild type granzyme B (SEQ ID NO: 1)

```
1       iigghvakph srpymaylmi wdqkslkrcg gflirddfvl taahcwgssi nvtlgahnik
61      eqeptqqfip vkraiphpay npknfsndim llqlerkakr travqplrlp snkaqvkpgq
121     tcsvagwgqt aplgkhshtl qevkmtvqed rkcesdlrhy ydstielcvg dpeikktsfk
181     gdsggplvcn kvaqgivsyg rnngmpprac tkvssfvhwi kktmkry
```

B) Nucleic acid sequence of wild type human granzyme B (SEQ ID NO: 2)

```
atcatcgggg gacatcaggc caagccccac tcccgcccct acatggcttt tcttatgatc    60
tgggatcaga agtctctgaa gaggtgcggt ggcttcctga taccagacga cttcgtgctg   120
acagctgctc actgttgggg aagctccata aatgtcacct tggcggccca caatatcaag   180
gaacaggagc cgacccagca gtttatccct gtgaaaagag ccatccccca tccagcctat   240
aatcctaaga acttctccaa tgacatcatg ctactgcagc tggagagaaa ggccaagcgg   300
accagagctg tgcagcccct caggctacct agcaacaagg cccaggtgaa gccagggcag   360
acatgcagtg tggccggctg gggcagacg gcccccctgg gaaaacactc acacacacta   420
caagaggtga agatgacagt gcaggaagat cgaaagtgcg aatctgactt acgccattat   480
tacgacagta ccattgagtt gtgcgtgggg gacccagaga ttaaaaagac ttcctttaag   540
ggggactctg gaggccctct tgtgtgtaac aaggtggccc aggcattgt ctcctatgga   600
cgaaacaatg gcatgcctcc acgagcctgc accaaagtct caagctttgt acactggata   660
aagaaaacca tgaaacgcta c                                             681
```

FIGURE 11

Nucleic acid sequences of improved granzyme B variants

A) Variant Gb R28K (SEQ ID NO: 3)

```
atcatcgggg gacatgaggc caagccccac tcccgcccct acatggcttt tcttatgatc 60
tgggatcaga agtctctgaa gaagtgcggt ggcttcctga tacgagacga cttcgtgctg 120
acagctgctc actgttgggg aagctccata aatgtcacct tgggggccca caatatcaag 180
gaacaggagc cgacccagca gtttatccct gtgaaaagag ccatccccca tccagcctat 240
aatcctaaga acttctccaa tgacatcatg ctactgcagc tggagagaaa ggccaagcgg 300
accagagctg tgcagcccct caggctacct agcaacaagg cccaggtgaa gccagggcag 360
acatgcagtg tggccggctg gggcagacg gcccccctgg gaaaacactc acacacacta 420
caagaggtga agatgacagt gcaggaagat cgaaagtgcg aatctgactt acgccattat 480
tacgacagta ccattgagtt gtgcgtgggg gacccagaga ttaaaaagac ttcctttaag 540
ggggactctg gaggccctct tgtgtgtaac aaggtggccc agggcattgt ctcctatgga 600
cgaaacaatg gcatgcctcc acgagcctgc accaaagtct caagctttgt acactggata 660
aagaaaacca tgaaacgcta c 681
```

B) Variant Gb R201A (SEQ ID NO: 4)

```
atcatcgggg gacatgaggc caagccccac tcccgcccct acatggcttt tcttatgatc 60
tgggatcaga agtctctgaa gaggtgcggt ggcttcctga tacgagacga cttcgtgctg 120
acagctgctc actgttgggg aagctccata aatgtcacct tgggggccca caatatcaag 180
gaacaggagc cgacccagca gtttatccct gtgaaaagag ccatccccca tccagcctat 240
aatcctaaga acttctccaa tgacatcatg ctactgcagc tggagagaaa ggccaagcgg 300
accagagctg tgcagcccct caggctacct agcaacaagg cccaggtgaa gccagggcag 360
acatgcagtg tggccggctg gggcagacg gcccccctgg gaaaacactc acacacacta 420
caagaggtga agatgacagt gcaggaagat cgaaagtgcg aatctgactt acgccattat 480
tacgacagta ccattgagtt gtgcgtgggg gacccagaga ttaaaaagac ttcctttaag 540
ggggactctg gaggccctct tgtgtgtaac aaggtggccc agggcattgt ctcctatgga 600
gcaaacaatg gcatgcctcc acgagcctgc accaaagtct caagctttgt acactggata 660
aagaaaacca tgaaacgcta c 681
```

C) Variant Gb R201K (SEQ ID NO: 5)

```
atcatcgggg gacatgaggc caagccccac tcccgcccct acatggcttt tcttatgatc 60
tgggatcaga agtctctgaa gaggtgcggt ggcttcctga tacgagacga cttcgtgctg 120
acagctgctc actgttgggg aagctccata aatgtcacct tgggggccca caatatcaag 180
gaacaggagc cgacccagca gtttatccct gtgaaaagag ccatccccca tccagcctat 240
aatcctaaga acttctccaa tgacatcatg ctactgcagc tggagagaaa ggccaagcgg 300
accagagctg tgcagcccct caggctacct agcaacaagg cccaggtgaa gccagggcag 360
acatgcagtg tggccggctg gggcagacg gcccccctgg gaaaacactc acacacacta 420
caagaggtga agatgacagt gcaggaagat cgaaagtgcg aatctgactt acgccattat 480
tacgacagta ccattgagtt gtgcgtgggg gacccagaga ttaaaaagac ttcctttaag 540
ggggactctg gaggccctct tgtgtgtaac aaggtggccc agggcattgt ctcctatgga 600
aagaacaatg gcatgcctcc acgagcctgc accaaagtct caagctttgt acactggata 660
aagaaaacca tgaaacgcta c 681
```

FIGURE 12

Amino acid sequences of improved variants of human wild type granzyme B

A) Variant with the substitution R28A (Gb R28A) (SEQ ID NO:6)

```
1     iigghvakph srpymaylmi wdqkslkacg gflirddfvl taahcwgssi nvtlgahnik
61    eqeptqqfip vkraiphpay npknfsndim llqlerkakr travqplrlp snkaqvkpgq
121   tcsvagwgqt aplgkhshtl qevkmtvqed rkcesdlrhy ydstielcvg dpeikktsfk
181   gdsggplvcn kvaqgivsyg rnngmpprac tkvssfvhwi kktmkry
```

B) Variant with the substitution R28K (Gb R28A) (SEQ ID NO:7)

```
1     iigghvakph srpymaylmi wdqkslkkcg gflirddfvl taahcwgssi nvtlgahnik
61    eqeptqqfip vkraiphpay npknfsndim llqlerkakr travqplrlp snkaqvkpgq
121   tcsvagwgqt aplgkhshtl qevkmtvqed rkcesdlrhy ydstielcvg dpeikktsfk
181   gdsggplvcn kvaqgivsyg rnngmpprac tkvssfvhwi kktmkry
```

C) Variant with the substitution R201A (Gb R201A) (SEQ ID NO:8)

```
1     iigghvakph srpymaylmi wdqkslkrcg gflirddfvl taahcwgssi nvtlgahnik
61    eqeptqqfip vkraiphpay npknfsndim llqlerkakr travqplrlp snkaqvkpgq
121   tcsvagwgqt aplgkhshtl qevkmtvqed rkcesdlrhy ydstielcvg dpeikktsfk
181   gdsggplvcn kvaqgivsyg anngmpprac tkvssfvhwi kktmkry
```

D) Variant with the substitution R201K (Gb R201K) (SEQ ID NO:9)

```
1     iigghvakph srpymaylmi wdqkslkrcg gflirddfvl taahcwgssi nvtlgahnik
61    eqeptqqfip vkraiphpay npknfsndim llqlerkakr travqplrlp snkaqvkpgq
121   tcsvagwgqt aplgkhshtl qevkmtvqed rkcesdlrhy ydstielcvg dpeikktsfk
181   gdsggplvcn kvaqgivsyg knngmpprac tkvssfvhwi kktmkry
```

FIGURE 13

Protein Sequence Alignment of Consensus Sequence for Wildtype Human Granzyme B

SEQ ID NO: 22: IIGGHVAKPH SRPYMAYLMI WDQKSLKRCG GFLIXDDFVL TAAHCWGSSI
SEQ ID NO: 23: IIGGHVAKPH SRPYMAYLMI WDQKSLKXCG GFLIRDDFVL TAAHCWGSSI

NVTLGAHNIK EQEPTQQFIP VKRXIPHPAY NPKNFSNDIM LLQLERKAKR
NVTLGAHNIK EQEPTQQFIP VKRAIPHPAY NPKNFSNDIM LLQLERKAKR

TRAVQPLRLP SNKAQVKPGQ TCSVAGWGQT APLGKHSHTL QEVKMTVQED
TRAVQPLRLP SNKAQVKPGQ TCSVAGWGQT APLGKHSHTL QEVKMTVQED

RKCESDLRHY YDSTIELCVG DPEIKKTSFK GDSGGPLVCN KVAQGIVSYG
RKCESDLRHY YDSTIELCVG DPEIKKTSFK GDSGGPLVCN KVAQGIVSYG

RNNGMPPRAC TKVSSFVHWI KKTMKRX
XNNGMPPRAC TKVSSFVHWI KKTMKRY

Alleles depicted as X in SEQ ID NO: 22

Position 35: X is Q or R
Position 74: X is P or A
Position 227: X is Y or H

Modifications depicted as X in SEQ ID NO: 23

Position 28: X is a modification
Position 201: X is a modification

FIGURE 14

Nucleic Acid Sequence Alignment of Consensus Sequence for wt Human Granzyme B

SEQ ID NO: 24: atcatcgggg gacatgaggc caagccccac tcccgcccct acatggcttt tcttatgatc tgggatcaga agtctctgaa gaggtgcggt
SEQ ID NO: 25: atcatcgggg gacatgaggc caagccccac tcccgcccct acatggcttt tcttatgatc tgggatcaga agtctctgaa gnnntgcggt ggcttcctgn nncgagacga cttcgtgctg acagctgctc actgttgggg aagctccata aatgtcacct tgggggccca caatatcaag
ggcttcctga tacgagacga cttcgtgctg acagctgctc actgttgggg aagctccata aatgtcacct tgggggccca caatatcaag gaacaggagc cgacccagca gtttatccct gtgaaaagan nnatccccca tccagcctat aatcctaaga acttctccaa tgacatcatg
gaacaggagc cgacccagca gtttatccct gtgaaaagag ccatccccca tccagcctat aatcctaaga acttctccaa tgacatcatg ctactgcagc tggagagaaa ggccaagcgg accagagctg tgcagcccct caggctacct agcaacaagg cccaggtgaa gccagggcag
ctactgcagc tggagagaaa ggccaagcgg accagagctg tgcagcccct caggctacct agcaacaagg cccaggtgaa gccagggcag acatgcagtg tggccggctg ggggcagacg gcccccctgg gaaaacactc acacacacta caagaggtga agatgacagt gcaggaagat
acatgcagtg tggccggctg ggggcagacg gcccccctgg gaaaacactc acacacacta caagaggtga agatgacagt gcaggaagat cgaaagtgcg aatctgactt acgccattat tacgacagta ccattgagtt gtgcgtgggg gacccagaga ttaaaaagac ttcctttaag
cgaaagtgcg aatctgactt acgccattat tacgacagta ccattgagtt gtgcgtgggg gacccagaga ttaaaaagac ttcctttaag ggggactctg gaggccctct tgtgtgtaac aaggtggccc agggcattgt ctcctatgga cgaaacaatg gcatgcctcc acgagcctgc
ggggactctg gaggccctct tgtgtgtaac aaggtggccc agggcattgt ctcctatgga nnnaacaatg gcatgcctcc acgagcctgc accaaagtct caagctttgt acactggata aagaaaacca tgaaacgcnn n
accaaagtct caagctttgt acactggata aagaaaacca tgaaacgcta c In SEQ ID NO: 24 nnn represents allele positions
In SEQ ID NO: 25 nnn represents modification positions

Apoptosis assay of Gb-Ki4(scFv) mutants on PI9$^+$ K562 target cell line

Result of Caspase 3/7 assay after incubation of CD30 positive target cell lines with Gb-Ki4(scFv) and Gb-Ki4(scFv) R201K

**Result of *ex vivo* experiments on primary material of leukemic patients using Gb-H22(scFv) and mutants**

FIGURE 18
**Result of *in vivo* experiments using Gb-Ki4(scFv) and Gb-Ki4(scFv) R201K**
(A)
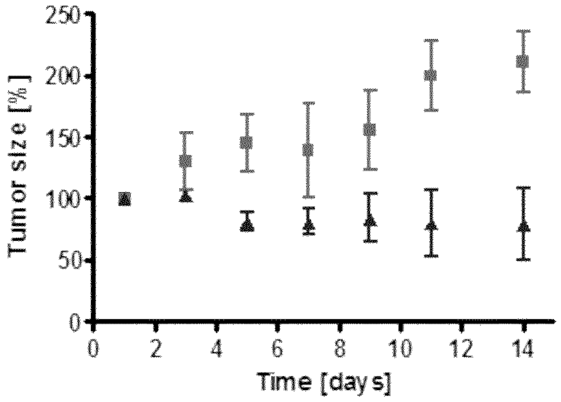
(B)
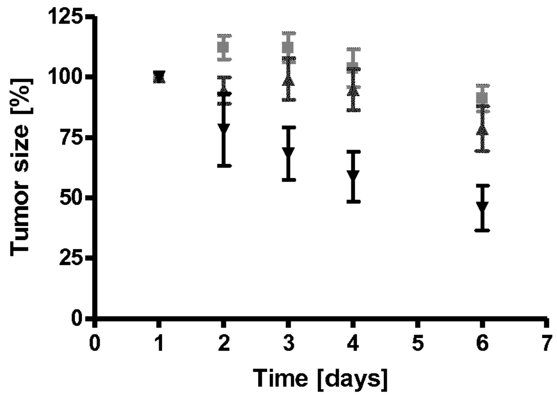

SEQUENCE LISTING

```
<160> NUMBER OF SEQ ID NOS: 21

<210> SEQ ID NO 1
<211> LENGTH: 227
<212> TYPE: PRT
<213> ORGANISM: Homo sapiens

<400> SEQUENCE: 1

Ile Ile Gly Gly His Val Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Arg Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Ala Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
```

-continued

```
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr
225


<210> SEQ ID NO 2
<211> LENGTH: 681
<212> TYPE: DNA
<213> ORGANISM: Homo sapiens

<400> SEQUENCE: 2

atcatcgggg gacatgaggc caagccccac tcccgcccct acatggcttt tcttatgatc     60

tgggatcaga agtctctgaa gaggtgcggt ggcttcctga tacgagacga cttcgtgctg    120

acagctgctc actgttgggg aagctccata aatgtcacct tgggggccca caatatcaag    180

gaacaggagc cgacccagca gtttatccct gtgaaaagag ccatccccca tccagcctat    240

aatcctaaga acttctccaa tgacatcatg ctactgcagc tggagagaaa ggccaagcgg    300

accagagctg tgcagcccct caggctacct agcaacaagg cccaggtgaa gccagggcag    360

acatgcagtg tggccggctg gggcagacg gcccccctgg gaaaacactc acacacacta    420

caagaggtga agatgacagt gcaggaagat cgaaagtgcg aatctgactt acgccattat    480

tacgacagta ccattgagtt gtgcgtgggg gacccagaga ttaaaaagac ttcctttaag    540

ggggactctg gaggccctct tgtgtgtaac aaggtggccc agggcattgt ctcctatgga    600

cgaaacaatg gcatgcctcc acgagcctgc accaaagtct caagctttgt acactggata    660

aagaaaacca tgaaacgcta c                                              681


<210> SEQ ID NO 3
<211> LENGTH: 681
<212> TYPE: DNA
<213> ORGANISM: Artificial Sequence
<220> FEATURE:
<223> OTHER INFORMATION: Human granzyme B: Variant Gb R28K

<400> SEQUENCE: 3

atcatcgggg gacatgaggc caagccccac tcccgcccct acatggcttt tcttatgatc     60

tgggatcaga agtctctgaa gaagtgcggt ggcttcctga tacgagacga cttcgtgctg    120

acagctgctc actgttgggg aagctccata aatgtcacct tgggggccca caatatcaag    180

gaacaggagc cgacccagca gtttatccct gtgaaaagag ccatccccca tccagcctat    240

aatcctaaga acttctccaa tgacatcatg ctactgcagc tggagagaaa ggccaagcgg    300

accagagctg tgcagcccct caggctacct agcaacaagg cccaggtgaa gccagggcag    360
```

acatgcagtg tggccggctg ggggcagacg gcccccctgg gaaaacactc acacacacta 420
caagaggtga agatgacagt gcaggaagat cgaaagtgcg aatctgactt acgccattat 480
tacgacagta ccattgagtt gtgcgtgggg gacccagaga ttaaaaagac ttcctttaag 540
ggggactctg gaggccctct tgtgtgtaac aaggtggccc agggcattgt ctcctatgga 600
cgaaacaatg gcatgcctcc acgagcctgc accaaagtct caagctttgt acactggata 660
aagaaaacca tgaaacgcta c 681

<210> SEQ ID NO 4
<211> LENGTH: 681
<212> TYPE: DNA
<213> ORGANISM: Artificial Sequence
<220> FEATURE:
<223> OTHER INFORMATION: Human granzyme B: Variant Gb R201A

<400> SEQUENCE: 4
atcatcgggg gacatgaggc caagccccac tcccgcccct acatggcttt tcttatgatc 60
tgggatcaga agtctctgaa gaggtgcggt ggcttcctga tacgagacga cttcgtgctg 120
acagctgctc actgttgggg aagctccata aatgtcacct tgggggccca caatatcaag 180
gaacaggagc cgacccagca gtttatccct gtgaaaagag ccatccccca tccagcctat 240
aatcctaaga acttctccaa tgacatcatg ctactgcagc tggagagaaa ggccaagcgg 300
accagagctg tgcagcccct caggctacct agcaacaagg cccaggtgaa gccagggcag 360
acatgcagtg tggccggctg ggggcagacg gcccccctgg gaaaacactc acacacacta 420
caagaggtga agatgacagt gcaggaagat cgaaagtgcg aatctgactt acgccattat 480
tacgacagta ccattgagtt gtgcgtgggg gacccagaga ttaaaaagac ttcctttaag 540
ggggactctg gaggccctct tgtgtgtaac aaggtggccc agggcattgt ctcctatgga 600
gcaaacaatg gcatgcctcc acgagcctgc accaaagtct caagctttgt acactggata 660
aagaaaacca tgaaacgcta c 681

<210> SEQ ID NO 5
<211> LENGTH: 681
<212> TYPE: DNA
<213> ORGANISM: Artificial Sequence
<220> FEATURE:
<223> OTHER INFORMATION: Human granzyme B: Variant Gb R201K

<400> SEQUENCE: 5
atcatcgggg gacatgaggc caagccccac tcccgcccct acatggcttt tcttatgatc 60
tgggatcaga agtctctgaa gaggtgcggt ggcttcctga tacgagacga cttcgtgctg 120
acagctgctc actgttgggg aagctccata aatgtcacct tgggggccca caatatcaag 180
gaacaggagc cgacccagca gtttatccct gtgaaaagag ccatccccca tccagcctat 240
aatcctaaga acttctccaa tgacatcatg ctactgcagc tggagagaaa ggccaagcgg 300
accagagctg tgcagcccct caggctacct agcaacaagg cccaggtgaa gccagggcag 360
acatgcagtg tggccggctg ggggcagacg gcccccctgg gaaaacactc acacacacta 420
caagaggtga agatgacagt gcaggaagat cgaaagtgcg aatctgactt acgccattat 480
tacgacagta ccattgagtt gtgcgtgggg gacccagaga ttaaaaagac ttcctttaag 540
ggggactctg gaggccctct tgtgtgtaac aaggtggccc agggcattgt ctcctatgga 600
aagaacaatg gcatgcctcc acgagcctgc accaaagtct caagctttgt acactggata 660

-continued

```
aagaaaacca tgaaacgcta c                                               681


<210> SEQ ID NO 6
<211> LENGTH: 227
<212> TYPE: PRT
<213> ORGANISM: Artificial Sequence
<220> FEATURE:
<223> OTHER INFORMATION: Human granzyme B: Variant Gb R28A

<400> SEQUENCE: 6

Ile Ile Gly Gly His Val Ala Lys Pro His Ser Arg Pro Tyr Met Ala
1               5                   10                  15

Tyr Leu Met Ile Trp Asp Gln Lys Ser Leu Lys Ala Cys Gly Gly Phe
            20                  25                  30

Leu Ile Arg Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Ala Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr
225


<210> SEQ ID NO 7
<211> LENGTH: 227
<212> TYPE: PRT
<213> ORGANISM: Artificial Sequence
<220> FEATURE:
<223> OTHER INFORMATION: Human granzyme B: Variant Gb R28K

<400> SEQUENCE: 7

Ile Ile Gly Gly His Val Ala Lys Pro His Ser Arg Pro Tyr Met Ala
1               5                   10                  15

Tyr Leu Met Ile Trp Asp Gln Lys Ser Leu Lys Lys Cys Gly Gly Phe
            20                  25                  30

Leu Ile Arg Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60
```

-continued

Thr Gln Gln Phe Ile Pro Val Lys Arg Ala Ile Pro His Pro Ala Tyr
65 70 75 80

Asn Pro Lys Asn Phe Ser Asn Asp Ile Met Leu Leu Gln Leu Glu Arg
85 90 95

Lys Ala Lys Arg Thr Arg Ala Val Gln Pro Leu Arg Leu Pro Ser Asn
100 105 110

Lys Ala Gln Val Lys Pro Gly Gln Thr Cys Ser Val Ala Gly Trp Gly
115 120 125

Gln Thr Ala Pro Leu Gly Lys His Ser His Thr Leu Gln Glu Val Lys
130 135 140

Met Thr Val Gln Glu Asp Arg Lys Cys Glu Ser Asp Leu Arg His Tyr
145 150 155 160

Tyr Asp Ser Thr Ile Glu Leu Cys Val Gly Asp Pro Glu Ile Lys Lys
165 170 175

Thr Ser Phe Lys Gly Asp Ser Gly Gly Pro Leu Val Cys Asn Lys Val
180 185 190

Ala Gln Gly Ile Val Ser Tyr Gly Arg Asn Asn Gly Met Pro Pro Arg
195 200 205

Ala Cys Thr Lys Val Ser Ser Phe Val His Trp Ile Lys Lys Thr Met
210 215 220

Lys Arg Tyr
225

<210> SEQ ID NO 8
<211> LENGTH: 227
<212> TYPE: PRT
<213> ORGANISM: Artificial Sequence
<220> FEATURE:
<223> OTHER INFORMATION: Human granzyme B: Variant R201A

<400> SEQUENCE: 8

Ile Ile Gly Gly His Val Ala Lys Pro His Ser Arg Pro Tyr Met Ala
1 5 10 15

Tyr Leu Met Ile Trp Asp Gln Lys Ser Leu Lys Arg Cys Gly Gly Phe
20 25 30

Leu Ile Arg Asp Asp Phe Val Leu Thr Ala Ala His Cys Trp Gly Ser
35 40 45

Ser Ile Asn Val Thr Leu Gly Ala His Asn Ile Lys Glu Gln Glu Pro
50 55 60

Thr Gln Gln Phe Ile Pro Val Lys Arg Ala Ile Pro His Pro Ala Tyr
65 70 75 80

Asn Pro Lys Asn Phe Ser Asn Asp Ile Met Leu Leu Gln Leu Glu Arg
85 90 95

Lys Ala Lys Arg Thr Arg Ala Val Gln Pro Leu Arg Leu Pro Ser Asn
100 105 110

Lys Ala Gln Val Lys Pro Gly Gln Thr Cys Ser Val Ala Gly Trp Gly
115 120 125

Gln Thr Ala Pro Leu Gly Lys His Ser His Thr Leu Gln Glu Val Lys
130 135 140

Met Thr Val Gln Glu Asp Arg Lys Cys Glu Ser Asp Leu Arg His Tyr
145 150 155 160

Tyr Asp Ser Thr Ile Glu Leu Cys Val Gly Asp Pro Glu Ile Lys Lys
165 170 175

Thr Ser Phe Lys Gly Asp Ser Gly Gly Pro Leu Val Cys Asn Lys Val
180 185 190

-continued

```
Ala Gln Gly Ile Val Ser Tyr Gly Ala Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr
225


<210> SEQ ID NO 9
<211> LENGTH: 227
<212> TYPE: PRT
<213> ORGANISM: Artificial Sequence
<220> FEATURE:
<223> OTHER INFORMATION: Human granzyme B: Variant Gb R201K

<400> SEQUENCE: 9

Ile Ile Gly Gly His Val Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Arg Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Ala Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Lys Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr
225


<210> SEQ ID NO 10
<211> LENGTH: 31
<212> TYPE: DNA
<213> ORGANISM: Artificial Sequence
<220> FEATURE:
<223> OTHER INFORMATION: 5' Primer R28K

<400> SEQUENCE: 10

cagaagtctc tgaagaagtg cggtggcttc c                                    31


<210> SEQ ID NO 11
<211> LENGTH: 31
```

<212> TYPE: DNA
<213> ORGANISM: Artificial Sequence
<220> FEATURE:
<223> OTHER INFORMATION: Reverse primer R28K

<400> SEQUENCE: 11
ggaagccacc gcacttcttc agagacttct g 31

<210> SEQ ID NO 12
<211> LENGTH: 31
<212> TYPE: DNA
<213> ORGANISM: Artificial Sequence
<220> FEATURE:
<223> OTHER INFORMATION: Forward primer R28A

<400> SEQUENCE: 12
cagaagtctc tgaaggcgtg cggtggcttc c 31

<210> SEQ ID NO 13
<211> LENGTH: 31
<212> TYPE: DNA
<213> ORGANISM: Artificial Sequence
<220> FEATURE:
<223> OTHER INFORMATION: Reverse primer R28A

<400> SEQUENCE: 13
ggaagccacc gcacgccttc agagacttct g 31

<210> SEQ ID NO 14
<211> LENGTH: 31
<212> TYPE: DNA
<213> ORGANISM: Artificial Sequence
<220> FEATURE:
<223> OTHER INFORMATION: Forward primer R28E

<400> SEQUENCE: 14
cagaagtctc tgaaggagtg cggtggcttc c 31

<210> SEQ ID NO 15
<211> LENGTH: 31
<212> TYPE: DNA
<213> ORGANISM: Artificial Sequence
<220> FEATURE:
<223> OTHER INFORMATION: Reverse primer R28E

<400> SEQUENCE: 15
ggaagccacc gcactccttc agagacttct g 31

<210> SEQ ID NO 16
<211> LENGTH: 30
<212> TYPE: DNA
<213> ORGANISM: Artificial Sequence
<220> FEATURE:
<223> OTHER INFORMATION: Forward primer R201K

<400> SEQUENCE: 16
ctcctatgga aagaacaatg gcatgcctcc 30

<210> SEQ ID NO 17
<211> LENGTH: 30
<212> TYPE: DNA
<213> ORGANISM: Artificial Sequence
<220> FEATURE:
<223> OTHER INFORMATION: Reverse primer R201K

<400> SEQUENCE: 17

-continued ggaggcatgc cattgttctt tccataggag 30

<210> SEQ ID NO 18
<211> LENGTH: 30
<212> TYPE: DNA
<213> ORGANISM: Artificial Sequence
<220> FEATURE:
<223> OTHER INFORMATION: Forward primer R201A

<400> SEQUENCE: 18
ctcctatgga gcaaacaatg gcatgcctcc 30

<210> SEQ ID NO 19
<211> LENGTH: 30
<212> TYPE: DNA
<213> ORGANISM: Artificial Sequence
<220> FEATURE:
<223> OTHER INFORMATION: Reverse primer R201A

<400> SEQUENCE: 19
ggaggcatgc cattgtttgc tccataggag 30

<210> SEQ ID NO 20
<211> LENGTH: 30
<212> TYPE: DNA
<213> ORGANISM: Artificial Sequence
<220> FEATURE:
<223> OTHER INFORMATION: Forward primer No. 2 R201K

<400> SEQUENCE: 20
ctcctatgga aagaacaatg gcatgcctcc 30

<210> SEQ ID NO 21
<211> LENGTH: 30
<212> TYPE: DNA
<213> ORGANISM: Artificial Sequence
<220> FEATURE:
<223> OTHER INFORMATION: Reverse primer No. 2 R201K

<400> SEQUENCE: 21
ggaggcatgc cattgttgtt tccataggag 30

GRANZYME B PROTEASE VARIANTS

REFERENCE TO SEQUENCE LISTING SUBMITTED ELECTRONICALLY

The official copy of the sequence listing is submitted electronically via EFS-Web as an ASCII formatted sequence listing as file "US14346600_2016_04_29 SEQID" created on 29 Apr. 2016, and having a size of 24 Kilobytes.

The sequence listing contained in this ASCII formatted document forms part of the specification and is herein incorporated by reference in its entirety.

FIELD OF THE DISCLOSURE

The technology provided herein relates to novel variants of enzymes exhibiting serine protease activity, more specifically to improved variants of the serine protease granzyme B; to nucleic acid molecules encoding said proteases, vectors, host cells containing the nucleic acids and methods for preparation and producing such enzymes; compositions and complexes comprising at least one of the proteases; and methods for using such enzymes as a part of an immunoprotease, in particular for the treatment of cancer.

BACKGROUND

In the treatment of tumors, autoimmune diseases, allergies and tissue rejection reactions, it is a disadvantage that the currently available medicaments, such as chemotherapeutic agents, corticosteroids and immunosuppressive agents, have a potential of side effects which is sometimes considerable, due to their relative non-specificity. It has been attempted to moderate this by various therapeutical concepts. Especially the use of immunotherapeutic agents is an approach, which resulted in an increase of the specificity of medicaments, especially in tumor treatment.

If the immunotherapeutic agent is an immunotoxin, then a monoclonal antibody (moAb) or an antibody fragment, which has a kinetic affinity for surface markers of tumor cells, is coupled with a cytotoxic reagent. If the immunotherapeutic agent is an anti-immunoconjugate for the treatment of autoimmune diseases, tissue rejection reactions or allergies, a structure relevant to pathogenesis or a fragment thereof is coupled to a toxin component. It has been found that immunotoxins can be characterized by a high immunogenicity in clinical use. This causes the formation of neutralizing antibodies in the patient, which inactivate the immunotoxin. Generally, a repeated and/or continuous administration of the therapeutic agents is unavoidable for long-term curative effects. This is particularly clear in the suppression of tissue rejection reactions after transplantations, or in the treatment of autoimmune diseases, due to the partly demonstrated genetically caused predisposition to a pathogenic autoimmune reaction.

The peptidic cell poisons which have been mostly used to date and are thus best characterized are the bacterial toxins diphtheria toxin (DT) (Beaumelle, B. et al. 1992; Chaudhary, V. et al. 1990; Kuzel, T. M. et al. 1993; LeMaistre, C. et al. 1998), *Pseudomonas* exotoxin A (PE) (Fitz Gerald, D. J. et al. 1988; Pai, L. H. and Pastan, I. 1998), and the plant-derived ricin-A (Engert, A. et al. 1997; Matthey, B. et al. 2000; O'Hare, M. et al. 1990; Schnell, R. et al. 2000; Thorpe, P. E. et al. 1988; Youle, R. J. and Neville, D. M. J. 1980). The mechanism of cytotoxic activity is the same in all of these toxins despite of their different evolutionary backgrounds. The catalytic domain inhibits protein biosynthesis by a modification of the elongation factor EF-2, which is important to translation, or of the ribosomes directly, so that EF-2 can no longer bind (Endo, Y. et al. 1987; Iglewski, B. H. and Kabat, D. 1975).

In most of the constructs employed to date, the systemic application of immunotoxins results in more or less strong side effects. In addition to the "vascular leak" syndrome (Baluna, R. and Vitetta, E. S. 1997; Schnell, R. et al. 1998; Vitetta, E. S. 2000), thrombocytopenia, hemolysis, renal insufficiency and sickness occur, depending on the construct employed and the applied dosage. Dose-dependent and reversible liver damage could also be observed (Battelli, M. G. et al. 1996; Grossbard, M. L. et al. 1993; Harkonen, S. et al. 1987). In addition to the documented side effects, the immunogenicity of the constructs employed to be observed in the use of the immunoconjugates or immunotoxins is the key problem of immunotherapy (Khazaeli, M. B. et al. 1994). This applies, in particular, to the humoral defense against the catalytic domains employed, such as ricin (HARA) (Grossbard, M. L. et al. 1998), PE (Kreitman, R. J. et al. 2000), or DT (LeMaistre, E. F. et al. 1992). Theoretically, all non-human structures can provoke an immune response. Thus, the repeated administration of immunotoxins and immunoconjugates is subject to limitations. A logical consequence of these problems is the development of human immunotoxins, now named human cytolytic fusion proteins (Rybak, S. et al. 1992).

WO 01/80880 A1 discloses the use of granzyme B as a human immunoprotease. The cytotoxic lymphocyte serine proteinase granzyme B induces apoptosis of abnormal cells by cleaving intracellular proteins at sites similar to those cleaved by caspases. However, granzyme B has a number of efficient natural inhibitors that prevent granzyme B-mediated apoptosis in certain cell types.

Therefore the availability of a human serine protease with improved apoptotic activity and reduced sensitivity towards activity-inhibiting substances would be highly advantageous.

SUMMARY OF THE DISCLOSURE

In a first aspect, embodiments of the disclosure provide polypeptides comprising a serine protease variant of wildtype human granzyme B, having a modification at one or more positions and showing increased apoptotic activity compared to wildtype granzyme B and reduced sensitivity to activity-inhibiting substances.

In a further aspect, embodiments of this disclosure relate to polypeptides comprising a serine protease variant of wildtype human granzyme B as shown in SEQ ID NO: 1, having a modification at one or more positions selected from the group of positions that correspond structurally or by amino acid sequence homology to the positions 28 and/or 201, or variants, modified forms, homologs, fusion proteins, functional equivalents or functional fragments thereof, wherein said polypeptide having a greater apoptotic activity compared to wildtype granzyme B and reduced sensitivity to activity-inhibiting substances.

In a further aspect, embodiments of this disclosure relate to polypeptides comprising a serine protease having at least 90% identity to amino acids 1-227 of SEQ ID NO: 1, and which, as compared to amino acids 1-227 of SEQ ID NO: 1, comprises at least one modification at one or more positions corresponding to position 28 and/or 201, or a modified form thereof, wherein said polypeptides having a greater apoptotic activity compared to wildtype granzyme B and reduced sensitivity to activity-inhibiting substances.

In still another aspect, embodiments of this disclosure provide nucleic acids encoding polypeptides variants with serine protease activity as disclosed herein, as well as vectors and host cells comprising such nucleic acids.

In other aspects, this disclosure relates to compositions comprising polypeptide variants as described herein, wherein the compositions may be useful for, or used in, therapeutical, cosmetic and/or diagnostic applications. In one advantageous embodiment, the composition is used as a therapeutical composition for the treatment of cancer.

In a further aspect, embodiments of this disclosure relate to methods for producing the polypeptide variants in a host cell by transforming the host cell with a DNA construct, advantageously including a promoter having transcriptional activity in the host cell, cultivating the transformed host cell in a suitable culture medium to allow expression of said protease and producing the protease. The method may also include recovering the produced protease.

In an advantageous embodiment of this disclosure, the polypeptide having serine protease activity has the nucleic acid sequence of SEQ ID NO: 3, SEQ ID NO: 4 or SEQ ID NO: 5 or variants, modified forms, homologs, fusion proteins, functional equivalents or functional fragments thereof.

The polypeptides according to present disclosure can be used for preparing a medicament for preventing or treating a disease like allergy, autoimmune reaction, tissue rejection reaction, or chronic inflammation reaction, in particular cancer.

In a further aspect, the disclosure relates to purified complexes comprising a binding structure and a polypeptide according to present disclosure, medicaments comprising such a complex in combination with a pharmacologically acceptable carrier or diluent and the use of such a complex for treating a malignant disease, an allergy, autoimmune reaction, tissue rejection reaction, or chronic inflammation reaction, in particular cancer.

Further, embodiments of this disclosure relate generally to the use of the polypeptides, compositions and complexes according to the present disclosure for the induction of cell death, in particular induction of cell death by apoptosis. Advantageously, polypeptides, compositions and complexes of this disclosure may be used for treating cancer.

Before the disclosure is described in detail, it is to be understood that this disclosure is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

To provide a comprehensive disclosure without unduly lengthening the specification, the applicant hereby incorporates by reference each of the patents and patent applications referenced above, in particular the disclosure of WO 01/80880 A2 and US 2009/0081185 A1.

BRIEF DESCRIPTION OF THE DRAWINGS

FIG. 1 shows examples for fusion proteins including granzyme B variants.

FIG. 7 shows the results of an apoptosis assay of Gb-Ki4 (scFv) variants on target cell line L1236: flow cytomery (Dotplots).

FIG. 8 shows diagrams with the results of an apoptosis assay of Gb-Ki4(scFv) variants on $PI9^+$ L1236 target cells.

FIG. 9 shows the results of an apoptosis assay of Gb-Ki4 (scFv) variants on L428 target cell line.

FIG. 10 shows an amino acid sequence (A) and a nucleic acid sequence (B) of human wildtype granzyme B (SEQ ID NO: 1, SEQ ID NO: 2).

FIG. 11 shows nucleic acid sequences of improved granzyme B variants (SEQ ID NO: 3, SEQ ID NO: 4, SEQ ID NO: 5).

FIG. 12 shows amino acid sequences of improved granzyme B variants (SEQ ID NO: 6, SEQ ID NO: 7, SEQ ID NO: 8, SEQ ID NO: 9).

FIG. 13 shows a protein sequence alignment of consensus sequence for wildtype granzyme B comprising different alleles as well as the positions for modifications.

FIG. 14 shows a nucleic acid sequence alignment of consensus sequence for of human granzyme B wildtype.

FIG. 18 shows changes in tumor size in mice after cytolytic fusion protein treatment when using serine protease variant R201K, where Gb-Ki4(scFv) R201K treatment is depicted as black triangles, Gb-Ki4(scFv) is depicted as grey triangles, and Gb-H22(scFv) R201K is depicted as grey squares.

DETAILED DESCRIPTION OF THIS DISCLOSURE

Figure 2:
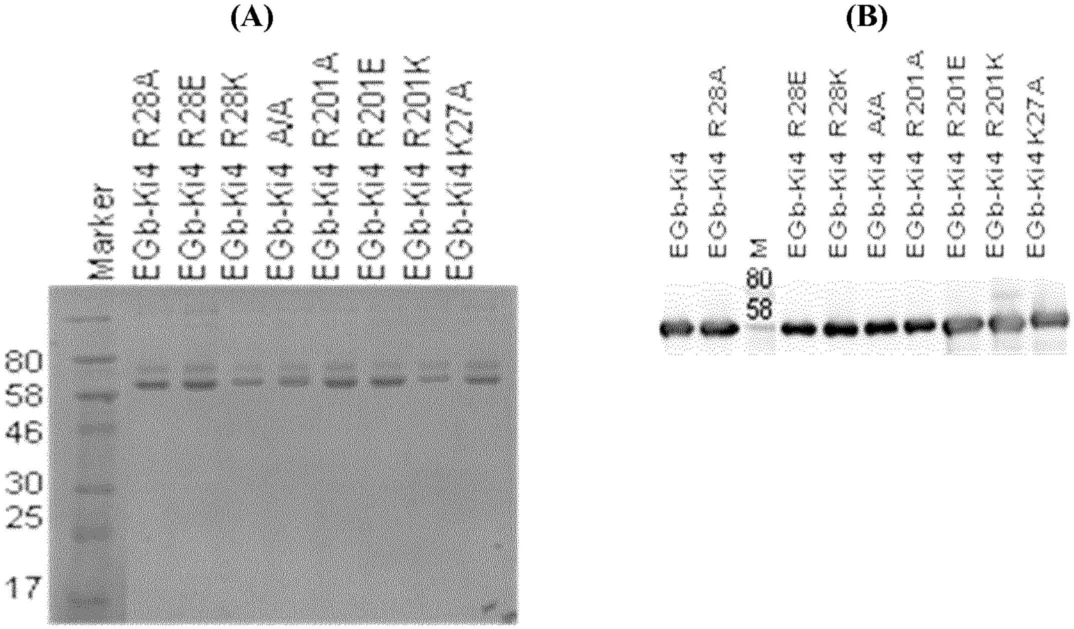
FIG. 2 shows the expression of granzyme B mutants in a Coomassie stained SDS-PAGE gel and Western Blot.

Disclosed herein are variants of the serine protease granzyme B and the use thereof for the treatment of various diseases.

In particular, serine protease variants according to the present disclosure showing increased proteolytic activity inducing cell apoptosis (apoptotic activity) compared to wildtype granzyme B enzymes and a reduced sensitivity to activity-inhibiting substances like Serpin B9 These characteristics make them specifically useful as a part of a powerful cytolytic fusion protein, in particular as a part of a complex according to the present disclosure. In particular, the serine protease variants according to the present disclosure showing a greater apoptotic activity compared to wild type granzyme B due to the reduced sensitivity to the activity-inhibiting substance Serpin B9.

The present disclosure reveals enzymes with an amino-acid sequence derived from the amino acid sequence shown in SEQ ID NO:1 or variants, modified forms, homologs, fusion proteins, functional equivalents or functional fragments thereof, having one or more modifications at one or more positions selected from the group of positions that correspond structurally or by amino acid sequence homology to the positions 28 and/or 201.

The term "modified form" or "variant" means that the enzyme has been modified from its original form (parent/wildtype, wt) but retains the same enzymatic functional characteristics as that of human wildtype granzyme B.

The term "fusion proteins" comprises all proteins derived from the human wildtype granzyme B or any variant thereof by covalently fusing additional amino-acid sequences at the C- and/or N-terminus. The source and composition of the additional amino-acid sequence is either natural from any living organisms or virus or unnatural. In particular, the fusion protein may be a "recombinant" polypeptide, which is defined either by its method of production or its structure. In reference to its method of production, e.g., a product made by a process, the process involved uses of recombinant nucleic acid techniques. In reference to structure, recombinant polynucleotides or polypeptides contain sequences from different sources. In particular, it encompasses polypeptides made by generating a sequence comprising two or more fragments which are not naturally contiguous or operably linked to each other. Thus, for example, products made by transforming cells with any unnaturally occurring vector are encompassed.

The term "functional fragment" or "effective fragment" means a fragment or portion of the human wildtype granzyme B or derivative thereof that retains about the same enzymatic function or effect.

The term "homologous polypeptide" according to the present disclosure comprises any enzyme with a sequence identity of at least 70% or preferably at least 80%, 85%, 90%, 95%, 97% or 99% to the human wildtype granzyme B.

The term "polynucleotide" corresponds to any genetic material of any length and any sequence, comprising single-stranded and double-stranded DNA and RNA molecules, including regulatory elements, structural genes, groups of genes, plasmids, whole genomes and fragments thereof.

The term "position" in a polynucleotide or polypeptide refers to specific single bases or amino acids in the sequence of the polynucleotide or polypeptide, respectively.

The term "granzyme B variants" means any granzyme B molecule obtained by site-directed or random mutagenesis, insertion, deletion, recombination and/or any other protein engineering method, which leads to granzyme B that differ in their amino acid sequence from the human wildtype granzyme B. The terms "wildtype granzyme B", "wildtype enzyme", or "wildtype" in accordance with the disclosure describe a serine protease enzyme with an amino acid sequence found in nature or a fragment thereof.

The term "isolated" describes any molecule separated from its natural source.

The term "mutation" refers to the substitution or replacement of single or multiple nucleotide triplets, insertions or deletions of one or more codons, homologous or heterologous recombination between different genes, fusion of additional coding sequences at either end of the encoding sequence, or insertion of additional encoding sequences or any combination of these methods, which result in a polynucleic acid sequence encoding the desired protein. Thus, the term "mutations" also refers to all of the changes in the polypeptide sequence encoded by the polynucleic acid sequence modified by one or more of the above described changes. Amino acid residues are abbreviated according to the following Table 1 either in one- or in three-letter code.

The term "nucleic acid molecule" or "nucleic acid" is intended to indicate any single- or double stranded nucleic acid molecule of cDNA, genomic DNA, synthetic DNA or RNA, Peptide nucleic acid (PNA) or LNA origin The term "stringent conditions" relates to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion (or other salts) at pH 7.0 to 8.3 and the temperature is at least about 30° C. for short probes (e.g. 10 to 50 nucleotides) and at least about 60° C. for longer probes. Stringent conditions may also be achieved with the addition of destabilizing agents, such as formamide and the like.

The term "variant of the nucleic acid molecule" refers herein to a nucleic acid molecule which is substantially similar in structure and biological activity to a nucleic acid molecule according to one of the claimed sequences.

The term "homologue of the nucleic acid molecule" refers to a nucleic acid molecule the sequence of which has one or more nucleotides added, deleted, substituted or otherwise chemically modified in comparison to a nucleic acid molecule according to one of the claimed sequences, provided always that the homologue retains substantially the same binding properties as the latter.

The term "derivative" as used herein, refers to a nucleic acid molecule that has similar binding characteristics to a target nucleic acid sequence as a nucleic acid molecule according to one of the claimed sequences The term “immunotoxin” refers to a complex comprising a targeting portion linked to a bacterial/plant toxin.

The term “cytolytic fusion protein” or “human cytolytic fusion protein” refers to a complex of a targeting portion linked to a human enzyme.

The term “immunoprotease” refers to a complex of a targeting portion linked to a human protease.

The term “modification” as used herein, refers for example to substitutions, insertions or deletions of amino acid residues at specific positions in an amino acid sequence as well as the phosphorylation, acetylation like palmitoylation, methylation, sulphation, glycosylation, lipidation like isoprenylation, farnesylation, attachment of a fatty acid moiety, glypiation and/or ubiquitinylation of specific positions on the polypeptide, or combinations thereof.

TABLE 1

Amino acid abbreviations

| | Abbreviations | Amino acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Mutations or variations are described by use of the following nomenclature: position; substituted amino acid residue(s). According to this nomenclature, the substitution of, for instance, an alanine residue for a glycine residue at position 20 is indicated as 20G. When an amino acid residue at a given position is substituted with two or more alternative amino acid residues these residues are separated by a comma or a slash. For example, substitution of alanine at position 30 with either glycine or glutamic acid is indicated as 20G/E, or 20G, 20E.

Furthermore, the following nomenclature could also be used: amino acid residue in the protein scaffold; position; substituted amino acid residue(s). According to this nomenclature, the substitution of, for instance, an alanine residue for a glycine residue at position 20 is indicated as Ala20Gly or A20G, or 20G. The deletion of alanine in the same position is shown as Ala20* or A20*. The insertion of an additional amino acid residue (e.g. a glycine) is indicated as Ala20AlaGly or A20AG. The deletion of a consecutive stretch of amino acid residues (e.g. between alanine at position 20 and glycine at position 21) is indicated as Δ(Ala20-Gly21) or Δ(A20-G21). When a sequence contains a deletion in comparison to the parent protein used for numbering, an insertion in such a position (e.g. an alanine in the deleted position 20) is indicated as *20Ala or *20A. Multiple mutations are separated by a plus sign or a slash. For example, two mutations in positions 20 and 21 substituting alanine and glutamic acid for glycine and serine, respectively, are indicated as A20G+E21S or A20G/E21S. When an amino acid residue at a given position is substituted with two or more alternative amino acid residues these residues are separated by a comma or a slash. For example, substitution of alanine at position 30 with either glycine or glutamic acid is indicated as A20G,E or A20G/E, or A20G, A20E. When a position suitable for modification is identified herein without any specific modification being suggested, it is to be understood that any amino acid residue may be substituted for the amino acid residue present in the position. Thus, for instance, when a modification of an alanine in position 20 is mentioned but not specified, it is to be understood that the alanine may be deleted or substituted for any other amino acid residue (i.e. any one of R, N, D, C, Q, E, G, H, I, L, K, M, F, P, S, T, W, Y and V).

The terms “conservative mutation”, or “conservative substitution”, respectively, refer to an amino acid mutation that a person skilled in the art would consider a conservative to a first mutation. “Conservative” in this context means a similar amino acid in terms of the amino acid characteristics. If, for example, a mutation leads at a specific position to a substitution of a non-aliphatic amino acid residue (e.g. Ser) with an aliphatic amino acid residue (e.g. Leu) then a substitution at the same position with a different aliphatic amino acid (e.g. Ile or Val) is referred to as a conservative mutation. Further amino acid characteristics include size of the residue, hydrophobicity, polarity, charge, pK-value, and other amino acid characteristics known in the art. Accordingly, a conservative mutation may include substitution such as basic for basic, acidic for acidic, polar for polar etc. The sets of amino acids thus derived are likely to be conserved for structural reasons. These sets can be described in the form of a Venn diagram (Livingstone C. D. and Barton G. J. (1993) “Protein sequence alignments: a strategy for the hierarchical analysis of residue conservation” Comput. Appl Biosci. 9: 745-756; Taylor W. R. (1986) “The classification of amino acid conservation” J. Theor. Biol. 119; 205-218). Conservative substitutions may be made, for example, according to the table below which describes a generally accepted Venn diagram grouping of amino acids.

TABLE 2

Venn diagram grouping amino acids

| | Set | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

The term “plasmid”, “vector system” or “expression vector” means a construct capable of in vivo or in vitro expression. In the context of the present disclosure, these constructs may be used to introduce genes encoding enzymes into host cells.

The term “host cell” in relation to the present disclosure includes any cell that comprises either the nucleic acid molecule or an expression vector as described above and which is used in the recombinant production of an enzyme having the specific properties as defined herein or in the methods of the present disclosure.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in "Atlas of Protein Sequence and Structure", M. O. Dayhoff et., Suppl. 3:353-358, National Biomedical Research Foundation, Washington, D.C., which adapts the local homology algorithm of Smith and Waterman (1981) Advances in Appl. Math. 2:482-489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. An example of an algorithm that is suitable for determining sequence similarity is the BLAST algorithm, which is described in Altschul, et al., J. Mol. Biol. 215:403-410 (1990). Software for performing BLAST analyses is publicly available through the National Center for Biotechnology Information. Likewise, computer programs for determining percent homology are also readily available.

It is also understood that the present disclosure comprises all molecules that are derived from the polynucleotides of the disclosure and all variants thereof described in this application, by posttranslational processing compared to the genetically encoded amino acid sequence. These posttranslational modifications comprise, but are not limited to, proteolytic cleavage of N-terminal sequences such as leader and/or pro-sequences, proteolytic removal of C-terminal extensions, N- and/or O-glycosylation, lipidation, acylation, deamidation, pyroglutamate formation, phosphorylation and/or others, or any combination thereof, as they occur during production/expression by the native host or any suitable expression host. These post-translational modifications may or may not have an influence on the physical or enzymatic properties of the enzymes as explored herein.

In preferred embodiments of the present disclosure, the modified human granzyme B has a substitution at one or more of the positions 28 and/or 201, relative to the numbering of human wildtype granzyme B given in SEQ ID NO: 1. These positions are characterized in that mutagenesis of the enzyme at these positions leads to improvement in the desired enzyme characteristics.

In yet a further aspect, the disclosure relates to a nucleic acid molecule and to the use of a nucleic acid molecule selected from the group consisting of a) a nucleic acid molecule encoding a polypeptide according to the present disclosure;

b) a nucleic acid molecule encoding for a modified form of the polypeptide according to the present disclosure, preferably in which one or more amino acid residues are conservatively substituted;

c) a nucleic acid molecule that is a fraction, variant, homologue, derivative, or fragment of the nucleic acid molecule presented as SEQ ID NO:3, SEQ ID NO:4 and/or SEQ ID NO:5;

d) a nucleic acid molecule that is capable of hybridizing to any of the nucleic acid molecules of a)-c) under stringent conditions e) a nucleic acid molecule that is capable of hybridizing to the complement of any of the nucleic acid molecules of a)-d) under stringent conditions f) a nucleic acid molecule having a sequence identity of at least 95% with any of the nucleic acid molecules of a)-e) and encoding for a serine protease, g) a nucleic acid molecule having a sequence identity of at least 70% with any of the nucleic acid molecules of a)-f) and encoding for a serine protease, h) or a complement of any of the nucleic acid molecules of a)-g).

A nucleotide or nucleic acid is considered to hybridize to one of the above nucleotides if it is capable of hybridizing under conditions of medium stringency, more preferably high stringency, even more preferably under very high stringency conditions.

The nucleic acid molecule of the present disclosure may comprise nucleotide sequences that encode for SEQ ID NO:3, or an effective fragment thereof or a variant, modified form, homologue or derivative thereof.

In particular, the disclosure provides a plasmid or vector system comprising a nucleic acid sequence encoding a polypeptide as described herein or a homologue or derivative thereof.

When compared with human wildtype granzyme B serine protease, polypeptides of the disclosure are characterized inter alia by a lower inhibition of Serpin B9 and a higher apoptosis inducing potential in mammalian cells. In particular, the serine protease variants according to the present disclosure showing in cells or cell lines having Serpin B9 expression ($PI9^{+-}$cells) a greater apoptotic activity compared to wild type granzyme B due to the reduced sensitivity to the activity-inhibiting substance Serpin B9.

In an advantageous embodiment, the polypeptide according to the present disclosure comprise a serine protease variant of wildtype human granzyme B as shown in SEQ ID NO: 1, having one or more substitution, insertion or deletion at positions selected from the group of positions that correspond structurally or by amino acid sequence homology to the positions 28 and/or 201, or a modified form thereof, wherein said polypeptide having a greater apoptotic activity compared to wildtype granzyme B.

In particular, the polypeptide according to the present disclosure comprises a serine protease variant of wildtype human granzyme B (GB), a serine-dependent and aspartate-specific protease, or a derivative thereof. Granzyme B is a component of cellular immune defense which, upon activation of cytotoxic T cells (CTL) or natural killer cells (NK), is secreted from the cytotoxic granules of these cells (Kam, C. M. et al. 2000; Shresta, S. et al. 1998). Upon the perforin-dependent translocation of granzyme B into the cytoplasm of attacked cells, a proteolytic cascade is initiated which ends in the apoptosis of the target cell (Greenberg, A. H. 1996). The exact function of the perforin secreted along with granzyme B is still being discussed currently, but it is not capable of inducing apoptosis alone. In the cell membrane, perforin aggregates into 12-18 mers and thereby forms pores of 15-18 nm. Initially, it was considered that granzyme B gets into the cytoplasm of the target cells through these pores. However, the 32 kDa protein granzyme B is too large for such a passage. It is more probable to assume that, after granzyme B has bound to perforin and this complex is successively internalized, perforin supports the endosomal release of granzyme B (Jans, D. A. et al. 1996). In recent years, various proteins could be identified which are activated by GB-mediated cleavage are directly related to apoptosis. Thus, the GB-caused proteolytic activation of various procaspases, especially 3 and 8, could be documented in vitro (Fernandes-Alnemri, T. et al. 1996; Srinivasula, S. M. et al. 1996); these are counted with the central proteases in apoptosis (Nicholson, D. W. and Thornberry, N. A. 1997). Further cytotoxic activities are displayed by granzyme B in the nucleus. After having intruded the cytoplasms of the target cell, granzyme B is relatively quickly translocated into the nucleus in a caspase-dependent way (Pinkoski, M. J. et al. 2000). There, granzyme B is capable, for example, of cutting nuclear matrix antigen and poly(ADP-ribose) polymerase (Andrade, F. et al. 1998). A quick apoptosis could be observed in cells after granzyme B accumulated in the nucleus (Trapani, J. A. et al. 1998; Trapani, J. A. et al. 1998). More recent data prove the initiation of apoptosis through the direct proteolytic cleavage of Bid, a member of the Bcl-2 family having only one BH3 domain. After cleavage, the truncated form tBid becomes embedded in the mitochondrial membrane and depolarizes it. This induces the release of cytochrome c and an apoptosis-inducing factor from the mitochondria into the cytoplasm, which critically accelerated cell death (Sutton, V. R. et al. 2000). Further caspase-independent toxic properties of granzyme B could be described, the underlying mechanism still being uncleared (Beresford, P. J. et al. 1999; Sarin, A. et al. 1997).

Embodiments of the present disclosure pertains to polypeptides comprising a serine protease having at least 90 percent identity to amino acids 1-227 of SEQ ID NO: 1, and which, as compared to amino acids 1-227 of SEQ ID NO: 1, comprises at least one substitution, insertion or deletion at one or more positions corresponding to position 28 or 201, or a modified form thereof.

Further embodiments of the present disclosure pertain to polypeptides comprising a serine protease having at least 85%, at least 90%, at least 95, at least 99 percent identity to amino acids 28-202 of SEQ ID NO: 1, whereby at one or more positions corresponding to position 28 or 201 is a modification. In particular the modification is a substitution and the substitution is selected from the group consisting of R201A, R201K and R28K, or any combinations thereof.

In the prior art, granzyme B alleles with different alleles encoding three amino acid substitutions were identified. Therefore, the sequence of wildtype granzyme B (SEQ ID NO. 1) comprises all these alleles. In particular, the three substitutions could be at positions 35, 74 and 227. In some embodiments, the substitutions are selected from the group consisting of Q35R, P74A and Y227H. In the coding nucleic acid sequence of human wildtype granzyme B the substitutions are in exon 2, an A→G substitution resulted in the mutation of glutamine (CAA) 48 (numbering with reference to Estebanez-Perpina et al., Biol. Chem., Vol. 381, pp. 1203-1214, December 2000) to arginine (CGA); in exon 3, a C→G substitution changed proline 88 (CCC) to alanine (GCC); and in exon 5, a T→C substitution altered tyrosine 245 (TAC), the last amino acid in the protein, to histidine (CAC).

Therefore, in further advantageous embodiments, polypeptides according to the present disclosure comprise in additional to the variations at one or more positions corresponding to position 28 or 201 a variation at one or more positions corresponding to position 35, 74 and/or 227 corresponding to the position of the amino acid sequence of SEQ ID NO: 1. For example, the variation at position 35 is 35R, the variation at position 74 is 74A and the variation at position 227 is 227H.

In further advantageous embodiments, the polypeptides according to the present disclosure comprise a substitution, insertion or deletion is at position 28 and/or 201. In one embodiment, the polypeptides comprise at least a substitution at position 28 and/or 201. In advantageous embodiments, the substitution is selected from the group consisting of R28A, R28E, R28K, R201A, R201E and R201K, in particular at least one of the substitutions R201A, R201K or R28K or any combinations thereof.

In a further embodiment the polypeptides according to the present disclosure have reduced sensitivity towards activity-inhibiting substances.

Examples of activity-inhibiting substance are any substance that works as inhibitors for proteases, in particular for serine proteases, more particular for granzymes. In an advantageous embodiment according to the present disclosure, the activity-inhibiting substance is specific for granzyme B.

In some embodiments, the activity-inhibiting substance inhibits granzyme B activity, inhibits granzyme transcription, inhibits granzyme translation, increases granzyme degradation, or destabilizes granzyme. In other embodiments, the granzyme inhibitor inhibits granzyme function. The granzyme inhibitor can be a polypeptide, an anti-granzyme antibody, or a small molecule. In some specific embodiments, the polypeptide is a serpin. Serpins are endogenous serine protease inhibitors and some examples of serpin useful in the context of the present invention are SPI6, PI9, PI-6, monocyte neutrophil elastase inhibitor (MNIN), PI-8, and plasminogen activator inhibitor 2 (PAI-2). In an advantageous embodiment, the activity-inhibiting substance is serpin B9 (proteinase inhibitor 9 (PI-9)). Furthermore, in some embodiments, the activity-inhibiting substance is a virally encoded serpin, cytokine response modifier A (CrmA) of poxviruses and/or a 100 kDa assembly protein (Ad5-100K) of a human adenovirus, known as adenovirus type 5.

There is no requirement that the polypeptides of the present disclosure comprise a full-length native polypeptide sequence of a serine protease, in particular of granzyme B. Rather, the polypeptide can also have a sequence that is modified from a native polypeptide sequence using the techniques known to those of skill in the art and/or taught in this specification. In some particular embodiments, the polypeptide is an enzyme variant that comprises a sequence that has serine protease function. Those of ordinary skill in the art will understand that it is be possible to reduce, increase or decrease the number of amino acids in polypeptide variants according to the present disclosure, so long as the active site and activity of the polypeptide having serine protease activity are maintained. For example, there are a wide variety of variants that can be prepared to meet the needs according to the present disclosure and the teachings of this paragraph and the remainder of the specification can be used to prepare variants based on a large number of polypeptides that have granzyme activity.

Therefore, the disclosure pertains to modified form of the polypeptides according to the present disclosure which has at least a minimum percentage sequence identity and/or percent homology to the polypeptides according to the present disclosure, wherein the minimum percent identity and/or homology is at least 75%, at least 80%, at least 85%, at least 90%, at least 93%, at least 96%, at least 97%, at least 98% or at least 99%.

The polypeptides having serine protease activity according to the present disclosure may, in addition to the serine protease active center, comprise a leader segment. Typically, these leader segments will be positively charged amino acid segments that facilitate protein translocation into the cytosol of the cell. Examples of such sequences include, but are not limited to an IG-kappa leader sequence. Of course, it is possible for one of ordinary skill to design and test an almost unlimited number of leader sequences that can be used in the invention. In most cases, these sequences simply require a relatively short segment of primarily positively charged amino acids. For a general review of such leader sequences, one can review Ford et al. 2001.

Embodiments pertain also to compositions comprising the polypeptides of the present disclosure, in particular to pharmaceutical, diagnostic or cosmetic compositions.

The polypeptides according to the present disclosure can be used with a "pharmaceutically acceptable carrier" which includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. A pharmaceutically acceptable carrier is preferably formulated for administration to a human, although in certain embodiments it may be desirable to use a pharmaceutically acceptable carrier that is formulated for administration to a non-human animal, such as a canine, but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In advantageous embodiments, polypeptide according to the disclosure are used for preparing a medicament for preventing or treating a disease like allergy, autoimmune reaction, tissue rejection reaction, or chronic inflammation reaction, preferably cancer.

In another aspect, the disclosure pertains to complexes comprising a binding structure and a polypeptide according to the present disclosure. The complex according to the disclosure can be regarded as a heterologous complex which comprises at least two domains, i.e., one effector domain and one binding domain, in particular the complex comprises a fusion protein including a binding structure and a polypeptide according to the present disclosure.

In some further aspects, the binding structure has a binding activity for cellular surface structures. For example, the polypeptides may be provided in complex with a cell targeting moiety that is a moiety that binds to and/or is internalized by only a selected population of cells such as cells expressing a particular cellular receptor. Such a cell targeting may, for example, comprise an antibody, a growth factor, a hormone, a cytokine, an aptamer or an avimer that binds to a cell surface protein. As used herein the term antibody may refer to an IgA, IgM, IgE, IgG, a Fab, a F(ab')2, single chain antibody or paratope peptide. In certain cases, a cell targeting moiety of the invention may target a particular type of cells such as a retinal, endothelial, iris or neuronal cell. In still further aspects a cell targeting moiety of the invention may be defined as cancer cell binding moiety.

For example, in certain embodiments, the binding structures as cell targeting moieties for use in the current disclosure are antibodies. In general the term antibody includes, but is not limited to, polyclonal antibodies, monoclonal antibodies, single chain antibodies, humanized antibodies, minibodies, dibodies, tribodies as well as antibody fragments, such as Fab', Fab, F(ab')2, single domain antibodies and any mixture thereof, hi some cases it is preferred that the cell targeting moiety is a single chain antibody (scFv). In a related embodiment, the cell targeting domain may be an avimer polypeptide. Therefore, in certain cases the cell targeting constructs of the invention are fusion proteins comprising a polypeptide according to the present disclosure and a scFv or an avimer. In some very specific embodiments the cell targeting construct is a fusion protein comprising a polypeptide according to the present disclosure fused to a single chain antibody.

In certain aspects of the disclosure, a binding structure may be a growth factor. For example, transforming growth factor, epidermal growth factor, insulin-like growth factor, fibroblast growth factor, B lymphocyte stimulator (BLyS), heregulin, platelet-derived growth factor, vascular endothelial growth factor (VEGF), or hypoxia inducible factor may be used as a cell targeting moiety according to the disclosure. These growth factors enable the targeting of constructs to cells that express the cognate growth factor receptors.

In further aspects of the invention, a binding structure may be a hormone. Some examples of hormones for use in the disclosure include, but are not limited to, human chorionic gonadotropin, gonadotropin releasing hormone, an androgen, an estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, erythropoitin, calcitriol, calciferol, atrial-natriuretic peptide, gastrin, secretin, cholecystokinin, neuropeptide Y, ghrelin, PYY3-36, insulin-like growth factor-1, leptin, thrombopoietin, angiotensinogen, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, or IL-36.

As discussed above targeting constructs that comprise a hormone enable method of targeting cell populations that comprise extracellular receptors for the indicated hormone.

In yet further embodiments of the invention, binding structures may be cytokines. For example, IL1, IL2, IL3, IL4, IL5, IL6, IL7, IL8, IL9, IL10, ILI11, IL12, IL13, IL14, IL15, IL-16, IL-17, IL-18, granulocyte-colony stimulating factor, macrophage-colony stimulating factor, granulocyte-macrophage colony stimulating factor, leukemia inhibitory factor, erythropoietin, granulocyte macrophage colony stimulating factor, oncostatin M, leukemia inhibitory factor, IFN-GAMMA, IFN-ALPHA, IFN-BETA, LT-BETA, CD40 ligand, Fas ligand, CD27 ligand, CD30 ligand, 4-1BBL, TGF-BETA, IL Ialpha, IL-1 BETA, IL-1RA (Interleukin 1 receptor antagonist), MIF and IGIF (IFN-gamma inducing factor) may all be used as targeting moieties according to the disclosure.

In certain aspects of the disclosure the binding structure may be a cell-targeting moiety, in particular a cancer cell-targeting moiety. It is well known that certain types of cancer cells aberrantly express surface molecules that are unique as compared to surrounding tissue. Thus, cell-targeting moieties that bind to these surface molecules enable the targeted delivery of the polypeptides of the present disclosure specifically to the cancers cells. For example, a cell targeting moiety may bind to and be internalized by a lung, breast, brain, prostate, spleen, pancreatic, cervical, ovarian, head and neck, esophageal, liver, skin, kidney, leukemia, bone, testicular, colon or bladder cancer cell. The skilled artisan will understand that the effectiveness of cancer cell targeted polypeptides of the present disclosure may, in some cases, be contingent upon the expression or expression level of a particular cancer marker on the cancer cell. Thus, in certain aspects there is provided a method for treating a cancer with targeted polypeptides of the present disclosure comprising determining whether (or to what extent) the cancer cell expresses a particular cell surface marker and administering polypeptide targeted therapy (or another anticancer therapy) to the cancer cells depending on the expression level of a marker gene or polypeptide.

In advantageous embodiments, the binding structure of the complex belongs to the group of antigen binding polypeptides/proteins targeting cell type specific markers, in particular the binding structure is directed against cancer cell specific structures, disease specific structures of pathogenic substances or pathogenic matter or the binding structure is binding to soluble markers of disease/environment/food and feed safety or biodefense.

In particular, in advantageous embodiments the binding structure of the complex comprises moieties which are affinity moieties from affinity substances or affinity substances in their entirety selected from the group consisting of antibodies, antibody fragments, receptor ligands, enzyme substrates, lectins, cytokines, lymphokines, interleukins, angiogenic or virulence factors, allergens, peptidic allergens, recombinant allergens, allergen-idiotypical antibodies, autoimmune-provoking structures, tissue-rejection-inducing structures, immunoglobulin constant regions and their derivatives, mutants or combinations thereof. In further advantageous embodiments, the antibody fragment is a Fab, an scFv; a single domain, or a fragment thereof, a bis scFv, Fab2, Fab3, minibody, maxibody, diabody, triabody, tetrabody or tandab, in particular a single-chain variable fragment (scFv). For example, the scFv is specific for the CD64 receptor and/or for the CD30 receptor.

In some embodiments, the complex has one or more supplementary components S in addition to the binding structure and a polypeptide according to the present disclosure. From his former experience, the skilled person knows that additional features and properties can have a critical importance to the efficient preparation and/or effectiveness of the complexes according to the invention. Due to the distinctness of the diseases to be treated with the complexes according to the disclosure, an adaptation of the complexes to the respective particular circumstances may be necessary.

The component S may be selected from the group consisting of an inducible promoter capable of regulating synthetic performance, a leader sequence capable of controlling protein biosynthesis, His tag, affinity tag, translocation domain amphiphatic sequence capable of translocating an apoptotic agent into a target cell, and a synthetic pro-granzyme B amphiphatic sequence capable of intracellular activation of a granzyme.

In advantageous embodiments, the component S is a leader sequence for secretory expression and/or the component S is a enterokinase cleavage site enabling activation of a polypeptide according to the present disclosure and/or the component S is a HIS tag or affinity tag, enabling purification of the complex.

In a further embodiment of the invention there is provided an isolated nucleic acid sequence comprising sequence encoding a polypeptide as described supra. Thus, a nucleic acid sequence encoding any of the polypeptides or polypeptide fusion proteins described herein are also included as part of the instant invention. The skilled artisan will understand that a variety of nucleic acid sequence may be used to encode identical polypeptides in view of the degeneracy of genetic code. In certain cases for example the codon encoding any particular amino acid may be altered to improve cellular expression.

In preferred aspects, a nucleic acid sequence encoding a polypeptide of this disclosure is comprised in an expression cassette. As used herein the term “expression cassette” means that additional nucleic acids sequences are included that enable expression of the polypeptides in a cell, or more particularly in a eukaryotic cell. Such additional sequences may, for examples, comprise a promoter, an enhancer, intron sequences or a polyadenylation signal sequence.

In still further aspects of the disclosure a coding sequence for the polypeptides may be comprised in an expression vector such as a viral expression vector. Viral expression vectors for use according to the invention include but are not limited to adenovirus, adeno-associated virus, herpes virus, SV-40, retrovirus and vaccinia virus vector systems.

Thus, in a specific embodiment, there is provided a method for treating a patient with cancer comprising administering to the patient an effective amount of a therapeutic composition comprising a polypeptide according to the present disclosure or a nucleic acid expression vector encoding a polypeptide as described supra. In preferred aspects, methods described herein may be used to treat a human patient.

As described above, in certain aspects, the disclosure provides methods for treating cancer. Thus, in certain cases, described methods may be used to limit or reduce tumor cells by apoptosis thereby reducing tumor growth or metastasis. A variety of cancer types may be treated with methods of the present disclosure, for example a cancer for treatment may be a bladder, blood, bone, bone marrow, brain, breast, colon, esophagus, eye, gastrointestinal, gum, head, kidney, liver, lung, nasopharynx, neck, ovary, prostate, skin, stomach, testis, tongue, or uterus cancer. Furthermore additional anticancer therapies may be used in combination or in conjunction with methods of the invention. Such additional therapies may be administered before, after or concomitantly with methods of the disclosure. For example an additional anticancer therapy may be chemotherapy, surgical therapy, an immunotherapy or a radiation therapy.

It is contemplated that polypeptides, compositions and/or complexes of the disclosure may be administered to a patient locally or systemically. For example, methods of the invention may involve administering a composition topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, intraperitoneally, subcutaneously, subconjunctival, intravesicularlly, mucosally, intrapericardially, intraumbilically, intraocularally, orally, by inhalation, by injection, by infusion, by continuous infusion, by localized perfusion bathing target cells directly, via a catheter, or via a lavage.

Further, embodiments of this disclosure relate to the use of the polypeptides, compositions and complexes according to the present disclosure for the preparation of a pharmaceutical, diagnostic or cosmetic composition. In some embodiments, the disclosure pertains to medicaments comprising the complex of the disclosure in combination with a pharmacologically acceptable carrier or diluent as defined above.

In another aspect, the disclosure relates to methods of treating a malignant disease, an allergy, autoimmune reaction, tissue rejection reaction, or chronic inflammation reaction comprising administering an effective amount of the complex according to the present disclosure to a patient in need thereof.

For the example of the anti-CD30 apoptotic agent Ki4 (scFv)-granzyme B R28K (Gb-Ki4(scFv) R28K) and Ki4 (scFv)-granzyme B R201K (Gb-Ki4(scFv) R201K), the cytotoxic effectiveness of complexes based on the present disclosure could be proven for the example of the cell line L1236. The secretion of this functional complex from eukaryotic cells additionally demonstrates the potential suitability of the proteins according to the invention for a gene-therapeutic application.

Cellular compartments or host cells which synthesize complete complexes according to the disclosure or individual components thereof after transformation or transfection with the nucleic acid molecules or vectors according to the invention are also claimed according to the invention.

The cellular compartments or host cells according to the disclosure are of either prokaryotic origin, especially from *E. coli, B. subtilis, S. carnosus, S. coelicolor, Marinococcus* sp., or eukaryotic origin, especially from *Saccharomyces* sp., *Aspergillus* sp., *Spodoptera* sp., *P. pastoris*, primary or cultivated mammal cells, eukaryotic cell lines (e.g., CHO, Cos or 293) or plant systems (e.g. *N. tabacum*).

The following methods and examples are offered for illustrative purposes only, and are not intended to limit the scope of the present disclosure in any way.

METHODS AND EXAMPLES

In the following examples, materials and methods of the present disclosure are provided including the determination of catalytic properties of enzymes obtained by the method. It should be understood that these examples are for illustrative purpose only and are not to be construed as limiting this disclosure in any manner. All publications, patents, and patent applications cited herein are hereby incorporated by reference in their entirety for all purposes.

Example 1

Recombinant Techniques for Manufacturing a Complex Comprising Granzyme B Variants The construction of the pMS plasmids encoding the sequence of Gb-H22(scFv) has already been described (Stahnke et al., 2008). The construction of the Gb-Ki4(scFv) encoding plasmid has been cloned before as well in a comparable manner. In all figures, Ki4 and Ki4(scFv) is the abbreviation for Ki4(scFv).

Site directed mutagenisis was conducted by overlap extension PCR using specific primers during an SOE PCR. The primer pairs are shown in table 3 below with the corresponding mutations indicated.

TABLE 3

Mutagenesis Primer

| Variant | 5' Primer ID | 5' Primer sequence | 3' Primer ID | 3' Primer sequence |
|---------|--------------|--------------------|--------------|--------------------| 
| R28K | SEQ ID NO: 10 | cagaagtctc tgaag**aag**tg cggtggcttc c | SEQ ID NO 11 | ggaagccacc gca**ctt**cttc agagacttct g |
| R28A | SEQ ID NO: 12 | cagaagtctc tgaag**gcg**tg cggtggcttc c | SEQ ID NO: 13 | ggaagccacc gca**cgc**cttc agagacttct g |
| R28E | SEQ ID NO: 14 | cagaagtctc tgaag**gag**tg cggtggcttc c | SEQ ID NO: 14 | ggaagccacc gca**ctc**cttc agagacttct g |
| R201K | SEQ ID NO: 16 | ctcctatgga **aag**aacaatg gcatgcctcc | SEQ ID NO: 17 | ggaggcatgc cattgtt**ctt** tccataggag |
| R201A | SEQ ID NO: 18 | ctcctatgga **gca**aacaatg gcatgcctcc | SEQ ID NO: 19 | ggaggcatgc cattgtt**tgc** tccataggag |
| R201E | SEQ ID NO: 20 | ctcctatgga **gag**aacaatg gcatgcctcc | SEQ ID NO: 21 | ggaggcatgc cattgtt**ctc** tccataggag |

In the same manner the mutated Granzyme B variant K27A was generated which has been described before to have a lower affinity to PI9 (Sun, Whisstock et al. 2001).

The specificity of the binding partners of the cytolytic fusion proteins are as follows: H22(scFv) is a humanized single chain specific to Fc gamma rexceptor I (CD64) whereas the murine Ki4(scFv) binds to CD30. The 72 kDa glycoprotein CD64 (FcγRI) is the mediator of endocytosis and phagocytosis, antibody-dependent cellular cytotoxicity and production of cytokines and superoxide. It is involved in inflammatory diseases and also over-expressed on the surface of leukemic cells. CD30 is a glycosylated type I transmembrane protein and belongs to the tumor necrosis factor receptor superfamily. It turned out to be a promising target for the treatment of Hodgkin lymphoma in previous studies (Schwab, Stein et al. 1982; Gruss, Pinto et al. 1996).

FIG. 10 shows the amino acid sequence of granzyme B wildtype according to NCBI (AAA75490.1 GI: 181186) with the allele Q35R (or Q48R depending on numbering of amino acids; also compare RAH mutations due to different alleles described in Sun et al.: "Granzyme B encoded by the commonly occurring human RAH allele retains pro-apoptotic activity", 2004, The Journal of biological Chemistry, 279 (17), pp. 16907-16911).

Examples for fusion proteins comprising a granzyme B variant are shown in FIG. 1A and FIG. 1B. Both fusion proteins comprise pCMV as a constitutive CMV promoter; Igk as a eader sequence for secretory expression, ECS as a Enterokinase cleavage site for the in vitro activation of granzyme B, a $His_6$-Tag for affinity purification (H), IRES as an internal ribosome entry site for bicystronic reporter expression and EGFP as an enhanced green fluorescent protein coding region. The construct in FIG. 1A comprises H22 as a CD64 specific scFv and the construct of FIG. 1B comprises Ki4 (for Ki4(scFv)) as a CD30 specific scFv.

Example 2

Cell Lines and Primary Cells

The used cell lines L540, L428, L1236 and K562 and the expression cell line HEK293T (Graham et al., 1977) were kept in RPMI complex medium (RPMI 1640 plus GlutaMAX-I) supplemented with 10% (v/v) FCS and 100 μg/ml penicillin and streptomycin (abbreviated as R10) at 37° C. and 5% $CO_2$. After transfection of HEK293T cells 100 μg/ml Zeocin was added for selection purposes.

L428 (ACC-197), L540 (ACC-72) and L1236 (ACC-530) are Hodgkin derived cell lines. L1236 is established from the peripheral blood of a 34-year-old man with Hodgkin lymphoma (mixed cellularity, stage IV, refractory, terminal, third relapse) in 1994, L428 is established from the pleural effusion of a 37-year-old woman with Hodgkin lymphoma (stage IVB, nodular sclerosis, refractory, terminal) in 1978 and L540 is established from the bone marrow of a 20-year-old woman with Hodgkin lymphoma (nodular sclerosis; stage IVB, pre-terminal stage). L540cy (von Kalle, Wolf et al. 1992) have been re-cultivated after one passage of growth within mice. Their characteristics regarding sensitivity to granzyme B mediated cell death, PI9 expression, CD30 receptor expression have been tested to be the same as for L540. K562 (ACC-10) is established from the pleural effusion of a 53-year-old woman with chronic myeloid leukemia (CML) in blast crisis in 1970.

Primary cells from CMML (chronic myelomonocytic leukaemia) patients were obtained after informed consent and with the approval of the Clinical Research Ethics Board of the University of Aachen. Mononuclear cells were isolated from peripheral blood by density gradient centrifugation using Biocoll separating solution (Biochrom AG) and cultured in RPMI complex medium. For viability assays 200 U/ml Interferon γ was added for stimulation of CD64 expression.

Example 3

Detection of Serpin B9 in Tumour Cell Lines and Primary Tumour Cells Via Western Blot Analysis and Flow Cytometry For the detection of endogenous Serpin B9 expression within tumor cell lines or primary tumour cells from leukemic patients, $10^6$ cells were lysed within 50 μl lysis buffer (Phosphate buffered Saline (PBS) supplemented with 1% Triton X-100) for 30 minutes on ice. The cell lysate was cleared via centrifugation and the protein concentration determined with Bradford reagent (BioRad). 40 μg of total soluble protein was loaded on an SDS gel for western blot analysis. After electroblotting onto nitrocellulose membranes and blocking with PBST containing 2.5% milk powder, Serpin B9 was detected with anti-PI9 (Santa Cruz, clone 7D8) and GAM-PO and visualized by an enhanced chemoluminescence (ECL) system (BD BioScience). The membrane was washed with PBST before development.

In parallel, detection of endogenous Serpin B9 expression was analyzed via a FACSCalibur flow cytometer (Becton Dickinson). Therefore $10^6$ cells were washed with PBS and 500 μl Cytofix/Cytoperm (BD BioScience) was added in order to fix and permeabilize the cells. After incubation for 20 minutes on ice and washing of the cells, a blocking step was included with 5% BSA in 200 μl PBS for 20 minutes on ice. The cells were washed once with PBS+0.2% Tween-20 and incubated with the first antibody anti-PI9 (Santa Cruz, clone 7D8) for 30 minutes on ice. The second antibody GAM-FITC was added to the washed cells and incubated as mentioned above. The final washing step and resuspension of the cells was done in PBS+0.2% Tween-20. Thus, with the help of flow cytometric analysis the endogenous expression of Serpin B9 could be detected. For evaluation the mean fluorescence intensities (MFI, shift in fluorescence intensity of a population of cells during flow cytometry) were compared. Mean values and standard deviations could be calculated from three independent experiments. For the flow cytometric analysis the program CellQuest Version 3.3 (Becton Dickinson, Heidelberg) was used, for graphical determinations WinMDI 2.8 (1993-1998 Joseph Trotter) was applied.

Figure 3:
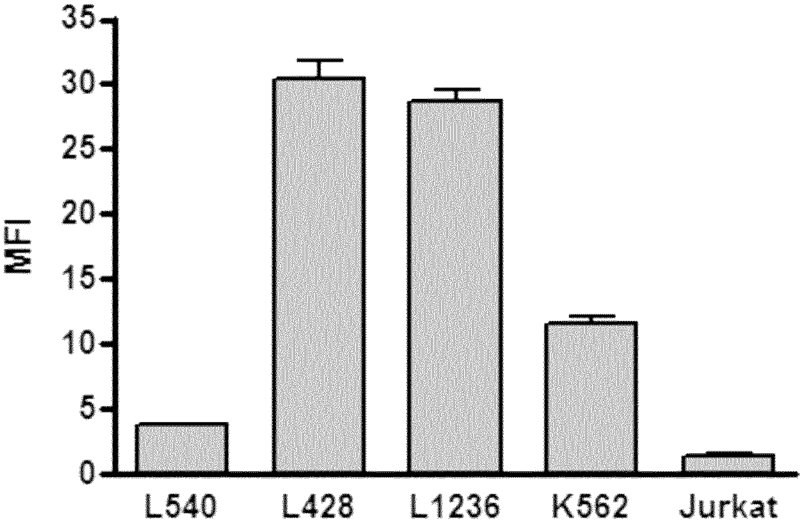
FIG. 3 shows the determination of endogeneous Serpin B9 in different cell lines via flow cytometric analysis. Mean Fluorescence Intensity (MFI) of detected Serpin B9 is compared between Hodgkin lymphoma derived cell lines (L428, K562, L1236) compared to control cell lines (L540, Jurkat).

FIG. 3 shows the results of the determination of endogenous Serpin B9 in different cell lines via flow cytometric analysis. The cells were analyzed for endogenous Serpin B9 expression as described above. The protein expression is the highest in L428 and L1236 compared to control cell lines Jurkat and L540 (same result for L540cy). The K562 cell line is also clearly PI9 positive. The measured fluorescence shift was quantified as MFI (Mean Fluorescence Intensity) and mean values were calculated (see above). The error bars indicate standard deviation from three independent experiments.

Figure 4:
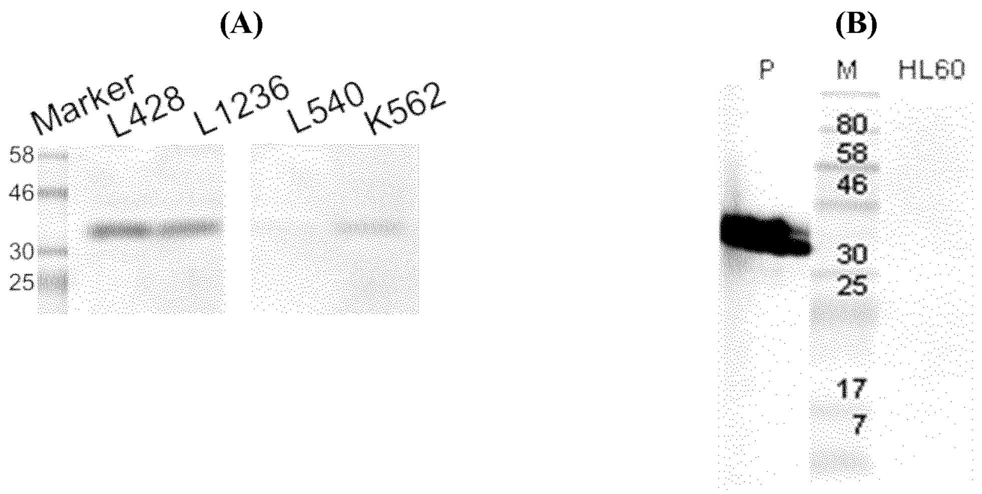
FIG. 4 shows the determination of Serpin B9 in different cell lines via western blot analysis. In panel (A), a western blot of Serpin B9 from Hodgkin lymphoma derived cell line (L428, L1236) is compared to control (L540, Jurkat). In panel (B), a western blot of Serpin B9 from human promyeloctyic leukemia (HL60) cell line is compared to positive control (recombinant PI9 from *E. coli*).

FIG. 4 shows the results of the determination of Serpin B9 expression in different cell lines (CD30 positive K562, L540, L428 and L1236 (A) and CD64 positive HL60 (B)) via western blot analysis. The cells were lysed as described above and 40 μg cell lysate was loaded on a 12% SDS gel. Serpin B9 was detected by specific anti-PI9 and GAM-PO and visualized by ECL. M: Marker in kDa, P: positive control (recombinant PI9 from *E. coli*). It can be seen that K562, L428 and L1236 clearly express Serpin B9 whereby K562 expresses the lowest amount.

Figure 17:
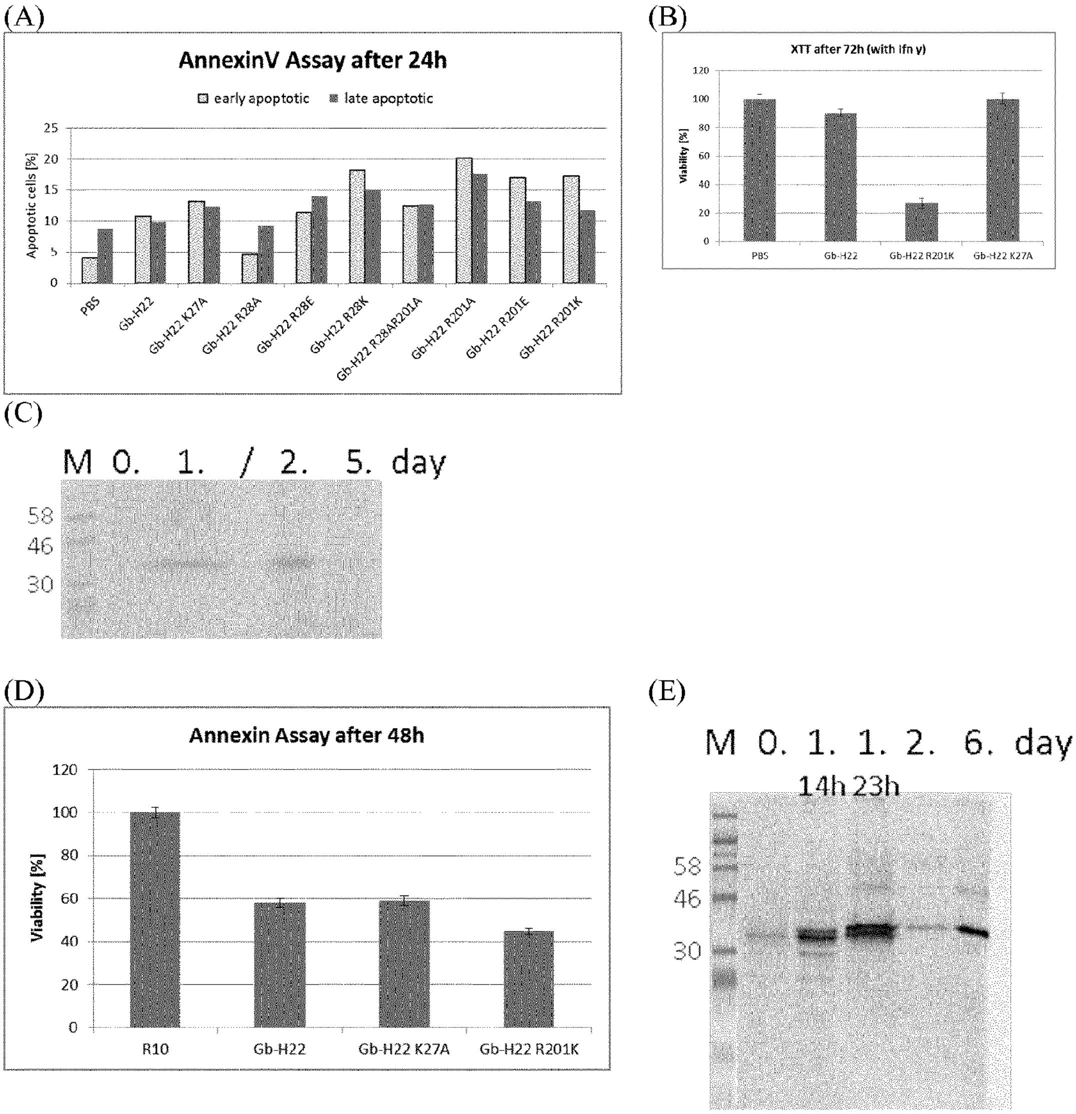
FIG. 17 shows the result of ex vivo experiments on primary material of leukemic patients using Gb-H22(scFv) and mutants. Panel (A) is a graph showing results from an Annexin V assay after 24 hours, which depicts percent apoptosis of primary leukemia cells when using the different serine protease variants. Panel (B) is a graph showing results from an XTT assay of primary leukemia cells, which measures percent viability after 72 hours of exposure to a cytolytic fusion protein when using different serine protease variants. Panel (C) is a photograph depicting a western blot of primary leukemia cells from Panels (A) and (B) for measurement of Serpin B9 over time. Panel (D) is a graph showing results from another Annexin V assay using primary cells from another leukemia patient, which depicts percent apoptosis when using different serine protease variants. Panel (E) is a photograph depicting a western blot of the primary cells used in Panel (D) for measurement of Serpin B9 over time.

FIGS. 17 (C) and (E) show the results of the determination of Serpin B9 expression in primary CMML cells via western blot analysis. The cells were lysed as described above and 40 μg cell lysate was loaded on a 12% SDS gel. Serpin B9 was detected by specific anti-PI9 and GAM-PO and visualized by ECL. M: Marker in kDa. It can be seen that primary cells also express the granzyme B inhibitor Serpin B9 during cultivation of the cells (days equal cultivation time).

Example 4

Protein Expression in Mammalian Cells and Purification

HEK293T cells were used as expression cell line. The cells were transfected with 1 μg DNA according to the manufacturer's instructions using RotiFect (Roth). The used pMS plasmid encodes for the bicistronic EGFP reporter so that expression of the target protein could be verified by the green fluorescence via fluorescence microscopy.

The secreted protein could be purified from the cell culture supernatant via Immobilized Metal-ion Affinity Chromatography (IMAC) and Fast Performance Liquid Chromatography (FPLC). The cleared supernatant was supplemented with 10 mM imidazole and loaded to an XK16/20 column (Amersham/GE Healthcare) containing 8 ml Sepharose 6 Fast Flow resin (Clontech/Takara). The used buffers such as incubation, washing and elution buffer were described before (Stocker, Tur et al. 2003). The eluted protein was re-buffered into 20 mM Tris, pH 7.4, 50 mM NaCl, concentrated, aliquoted and stored at −80° C. For activation prior to use Enterokinase was added to the protein (0.02 U/μg) with 2 mM $CaCl_2$ for 16 h incubation at 23° C. The protein concentration was calculated from Coomassie stained SDS gels using AIDA Image Analyzer Software. The purified proteins or cell lysates were analysed via SDS-PAGE under reducing conditions and Coomassie staining. Western blots were performed according to standard techniques.

FIG. 2 exemplary shows the expression of granzyme B mutants fused to the binder Ki4(scFv) in HEK293T cells after purification via affinity chromatography. 10 μl of elution fractions were loaded on a SDS-PAGE gel and protein was stained with Coomassie (A) or western blot was performed with anti-Gb/GAM-PO (B).

Example 5

Expression and Purification of Recombinant Serpin B9 in *E. coli*

For the expression of recombinant Serpin B9 the *E. coli* expression strain BL21 (DE3) was used for a 4 L fermentation in synthetic medium. The bacteria were harvested 24 h after induction with Isopropyl Thiogalactoside (IPTG). After centrifugation the bacterial pellet was re-suspended in lysis buffer (50 mM $NaH_2PO_4$, pH 8.0, 500 mM NaCl, 0.5 mM DTT) and sonicated six times for 60 s, 70%, 9 cycles. The supernatant was supplemented with 10 mM imidazol and purified via IMAC as described above. After a second affinity purification step, the protein was re-buffered into 20 mM Tris, pH 7.4, 1 mM DTT and further purified via anion exchange chromatography (Q-Sepharose XL, 1 ml, GE Healthcare) with a salt gradient of 0.05-1 M NaCl. In order to achieve satisfying purity, size exclusion chromatography (SEC) followed using a Superdex 75 (GE Healthcare) column in 20 mM Tris, pH 7.5, 50 mM NaCl, 1 mM DTT. The purified protein was used for complex formation experiments described in example 6.

Example 6

Complex Formation and Enzymatic Activity Measurements

The complex formation between recombinant Serpin B9 (see example 5) and Gb-H22(scFv) and its mutants took place in a 5:1 molar ratio under reducing conditions in 20 mM Tris, pH 7.4, 50 mM NaCl and 1 mM DTT. 600 ng wildtype or mutant Gb-H22(scFv) were incubated with or without Serpin B9 for 1 hour at 37° C. The remaining activity was detected by cleavage of 200 μM of the synthetic substrate Ac-IETD-pNA (Calbiochem/Merck) which mimics the cleavage site of Pro-caspase 3. The reaction was monitored in a microplate reader at 37° C. for one hour with 1 min interval with an absorbance of 405 nm. The velocity of the activity was calculated from the linear slope of the reaction in the first 10-12 minutes and converted to pmol/min with the help of the corresponding conversion factor ($\mu M/A_{405nm}$).

Figure 6:
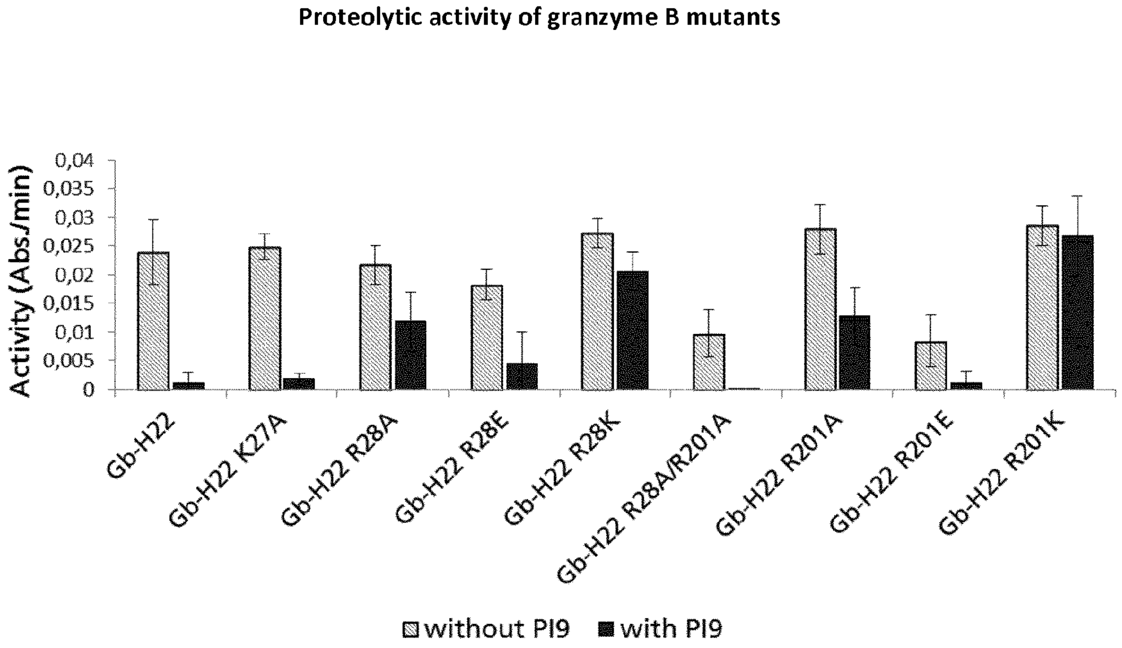
FIG. 6 illustrates the proteolytic activity of granzyme B variants in a diagram.

FIG. 6 shows the proteolytic activity of granzyme B variants, fused to H22(scFv) after pre-incubation with Serpin B9. It can be seen that the mutants Gb-H22(scFv) R28K and Gb-H22(scFv) R201K remain most of their activity in presence of PI9. Mean values (for calculation of activity see above) and standard deviations are based on three independent experiments.

Example 7

Binding Analysis

The binding of Gb-Ki4(scFv) mutants to the target cell lines L428 and L1236 was evaluated by flow cytometry. $4\times10^5$ cells were washed with PBS and incubated with 1 μg purified protein in 100 μl PBS for 30 minutes on ice. After 2 wash cycles (Dade Serocent) cells were incubated with anti-His Alexa 488 for 30 min on ice in the dark. Unbound antibodies were removed by washing with PBS. Specific binding was determined with the help of FACSCalibur flow cytometer (Becton Dickinson).

Figure 5:
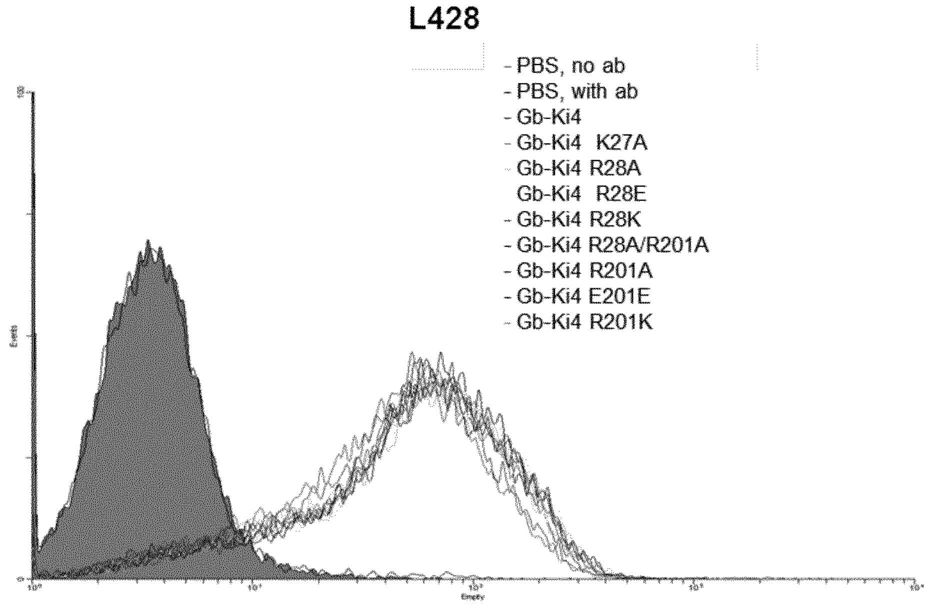
FIG. 5 is a diagram showing the specific binding of Gb-Ki4(scFv) mutants to target cells.

FIG. 5 shows the specific binding of Gb-Ki4(scFv) mutants to target cells. $10^5$ cells were incubated with 1 μg purified protein and detected with anti-His Alexa 488. The detection occurred via flow cytometry. Histogram shown exemplary for L428 (representative for L1236 and L540cy) (X: FL1, Y: events).

Example 8

Apoptosis and Viability Assay

Apoptosis was documented via AnnexinV/Propidium iodide (PI) staining. $2*10^5$ cell/ml were incubated at 37° C. and 5% $CO_2$ with 11.1 or 33.3 nM protein for 24 h, 48 h or 72 h in 12 well plates. After incubation, cells were washed in PBS and the pellet was re-suspended in 450 μl cell-free culture supernatant from HEK293T cells expressing AnnexinV-labelled green fluorescent protein (EGFP, (Stocker, Pardo et al. 2008)) supplemented with 10× AnnexinV binding buffer (100 mM HEPES, pH 7.5, 1.5 M NaCl, 50 mM KCl and 20 mM $CaCl_2$) as well as 5 μg/ml PI. The incubation took place for 20 minutes on ice in the dark and the analysis was done via flow cytometric measurements. FL1 channel (X axis) detects GFP fluorescence whereby FL3 channel (Y axis) determines PI. Explanation of corresponding dotplots: quadrant upper right=late apoptotic cells (AnnexinV and PI positive), quadrant upper left=necrotic cells (AnnexinV negative and PI positive), quadrant lower right=early apoptotic cells (AnnexinV positive and PI negative), quadrant lower left=viable cells (AnnexinV and PI negative).

The cytotoxic effect of Gb-Ki4(scFv) wildtype and its variants on CD30 positive cell lines or Gb-H22(scFv) wildtype and its variants on mononuclear cells from CMML patient material was monitored using the ability of metabolic active cells to reduce the tetrazolium salt XTT to orange colored compounds of formazan. The intensity of light was measured by a microplate reader and is directly proportional to the number of living cells. $2*10^5$ cells were plated in 1 ml of R10 in 12 well plates either in 1:5 serial dilutions or with a single protein concentration of 11 nM of the respective cytolytic fusion protein and incubated at 37° C. and 5% $CO_2$. After 48 or 72 hours incubation 100 μl of the cell suspension were transferred into 96 well plates and 50 μl XTT was added. Read out was done at 450 nm with reference wavelength of 650 nm.

In order to determine the Caspase 3/7 activity a pre-luminescent Caspase-3/7-DEVD-aminoluciferine substrate was used (Caspase-Glo™ 3/7 Assay, Promega). Caspase 3/7 is a direct substrate of Granzyme B. If it is cleaved after Granzyme B delivery into the target cells and thereby activated, it can cleave the substrate so that free unbound aminoluciferine is released. This is then used by luciferase whereby a luminescence signal is produced. Thus, the measured luminescence is directly proportional to the activity of caspase 3/7.

FIG. 7 and FIG. 8 show the results of the apoptosis assay by AnnexinV-GFP staining of Gb-Ki4(scFv) mutants on PI9 positive target cell line L1236. Results of three independent experiments are shown, either as dotplots (X: FL1, Y:FL3, explained above) or as bar graph (Y: Amount of pre and late apoptotic cells in relation to total cell population seen in dotplot of flow cytometric analysis or viability [%]). (FIG. 7A) 33.3 nM protein was added to cells, incubation for 48 h; (FIG. 7B) 11.1 nM protein was added to cells, incubation for 48 h; (FIG. 8A) 33.3 nM protein was added to cells, incubation for 72 h; (FIG. 8B) 11.1 nM protein was added to cells, incubation for 72 h. (FIG. 8C) 11.1 nM Gb-Ki4 (scFv) variants was added to $2*10^5$ cells in 1 ml for 48 hours at 37° C. Viability was determined via addition of 50 μl XTT to 100 μl cells after transfer into a 96 well plate. Negative control is with PBS buffer. Standard deviations are shown for 3 to 5 independent experiments. Statistical significance determined via student t-test: () for $p<0.05$, (*) for $p<0.001$. Results indicate an increased cytotoxic effect of the mutants compared to the wildtype and the mutant from literature (K27A). The most promising mutants from this example are Gb-Ki4(scFv) R28K comprising a modified granzyme B (SEQ ID NO: 1) with a substitution at position 28 from R to K, Gb-Ki4(scFv) R201A comprising a modified granzyme B (SEQ ID NO: 1) with a substitution at position 201 from R to A and Gb-Ki4(scFv) R201K comprising a modified granzyme B (SEQ ID NO: 1) with a substitution at position 201 from R to K.

FIG. 9 shows the results of an apoptosis assay of Gb-Ki4 (scFv) mutants on PI9 positive target cell line L428. Verification of apoptosis via AnnexinV-GFP assay (Clontech). Results of three independent experiments are shown, either as dotplots (X: FL1, Y:FL3, explained above) or as bar graph (Y: sum of pre and late apoptotic cells in relation to total cell population or viability [%]). (A) 33.3 nM protein was added to cells, incubation for 24 h; (B) 11.1 nM protein was added to cells, incubation for 48 h. (C) 11.1 nM Gb-Ki4(scFv) variants was added to $2*10^5$ cells in 1 ml for 48 hours at 37° C. Viability was determined via addition of 50 μl XTT to 100 μl cells after transfer into a 96 well plate. Negative control is with PBS buffer. Standard deviations are shown for 3 to 5 independent experiments. Statistical significance determined via student t-test: () for $p<0.05$ (*) for $p<0.001$. The most promising mutants are the same as described above for L1236.

Figure 15:
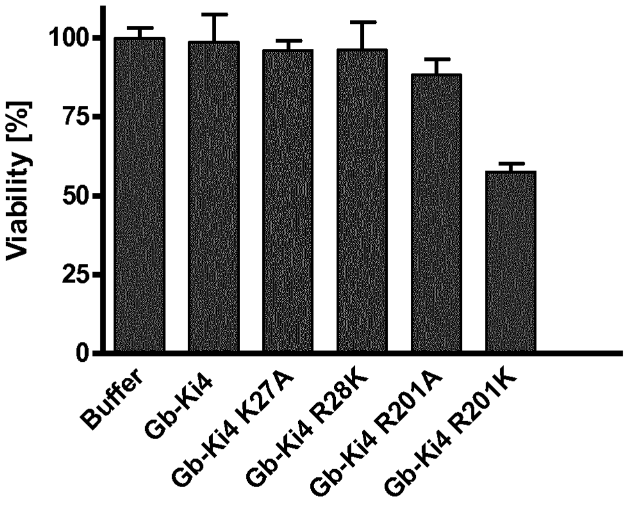
FIG. 15 is a bar graph showing the results of an apoptosis assay of Gb-Ki4(scFv) mutants on $PI9^+$ K562 target cell line.

FIG. 15 shows the viability of PI9 positive K562 cells after incubation with 11.1 nM cytolytic fusion protein for 48 hours at 37° C. Results of three independent experiments are shown as bar graph (Y: viability [%]). Gb-Ki4(scFv) R201K leads to the highest apoptotic rates. Viability was determined via addition of 50 μl XTT to 100 μl cells after transfer into a 96 well plate. Negative control is with PBS buffer. Standard deviations are shown for 3 to 5 independent experiments. Statistical significance determined via student t-test: () for $p<0.05$ (*) for $p<0.001$.

Figure 16:
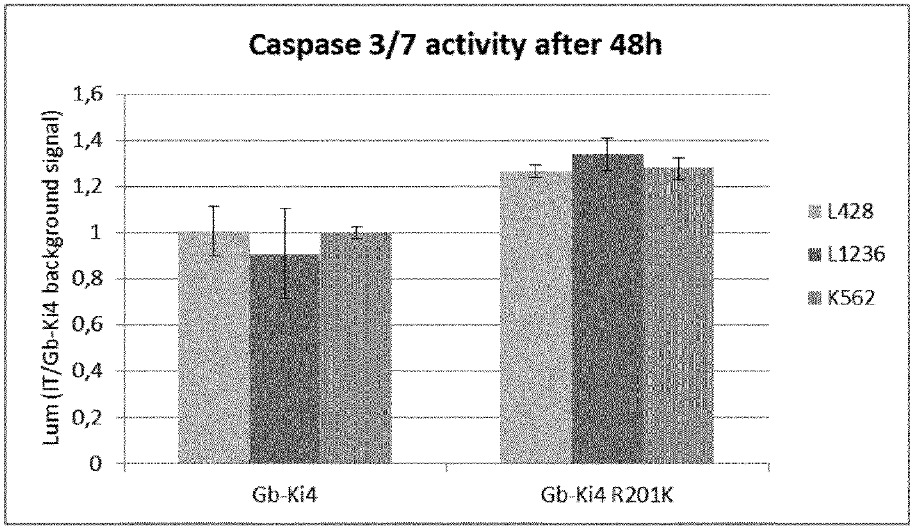
FIG. 16 is a bar graph showing the result of a Caspase 3/7 assay after incubation of CD30 positive target cell lines with Gb-Ki4(scFv) and Gb-Ki4(scFv) R201K.

FIG. 16 shows the caspase 3/7 activity after 48 hours incubation with 11.1 nM cytolytic fusion protein. Results of three independent experiments are shown as bar graph (Y: relation of luminescence of treated samples to background signal of Gb-Ki4(scFv) [−]). The R201K substitution resulted in a 22-25% increase in caspase 3/7 activity of Serpin B9 positive cell lines compared to the wildtype protein.

FIG. 17 shows results of apoptosis and viability assays on primary cells from leukemic patients and determination of their SerpinB9 expression. Results of three independent experiments are shown either as bar graph (Y: apoptotic cells [%] or viability [%]) or as western blot. (A) Results from AnnexinV Assay after incubation with 33 nM cytolytic fusion protein for 24 h. (B) Viability measurement of cells incubated for 72 hours with 33 nM cytolytic fusion protein determined via XTT. (C) Anti-SerpinB9 western blot of the used cells used in (A) and (B) (see example 2 for description of method). (D) Viability assay with cells from a different patient after incubation for 24 h with 33 nM cytolytic fusion protein. (E) Anti-SerpinB9 blot (see example 2) of the used cells from (D). The novel Serpin B9 resistant variants lead to highest apoptotic rates in comparison to the wildtype and the mutant from literature (K27A).

Example 9

Mouse Experiments

The experiments were officially approved by the local Animal Care and Use Review Committee. All animals received humane care in accordance with the requirements of the German Tierschutzgesetz, §8 Abs. 1 and in accordance with the Guide for the Care and Use of Laboratory Animals published by the National Institute of Health.

6- to 8-week-old female BALB/c nu/nu mice (Charles River, Germany) were used. For injection of PI9 positive tumor cells, L428 transfected with far red fluorescent protein Kat2 (pTag-Katushka2-N; Evrogen) were used after washing with PBS and resuspension in 50% BD Matrigel™ Basement Membrane Matrix High Concentration, Growth Factor Reduced (BD Bioscience). $5*10^6$ cells in 30 μl were injected subcutaneously in the right hind limb of 21 mice. Treatment was started one day after cell injection since previous experiments demonstrated immediate growth of the cells within the first week after injection. The mice were randomized into three groups of seven animals and obtained daily doses of 50 μg Gb-H22(scFv) R201K, Gb-Ki4(scFv) or Gb-Ki4(scFv) R201K respectively for 5 days. At the same time tumor growth measurements were performed via imaging as shown in former studies (Pardo, Stocker et al. 2012) with the CRi Maestro system (Cri Inc., Woburn, Mass., USA). Images were taken and analysed with the Maestro Spectral Imaging Software. In order to monitor the Kat2 signal of the transfected L428 cells, the yellow filter set (630-850 nm) was used. Treatment response with Gb-Ki4 (scFv) and Gb-Ki4(scFv) R201K was compared to the non-specific control group treated with Gb-H22(scFv) using one-tailed t-test (GraphPad Prism, Version 4.0c).

For injection of PI9 negative tumor cells, L540cy were used after washing with PBS and resuspension in 50% BD Matrigel™ Basement Membrane Matrix High Concentration, Growth Factor Reduced (BD Bioscience). $5*10^6$ cells were injected subcutaneously in a volume of 30 μl into the right hind limb of the mice. Treatment was started when tumor size was 3 to 5 mm. Tumor size was determined via triplicate caliper measurements. The mice were randomized into two groups and obtained 50 μg Gb-H22(scFv) R201K (n=3) or Gb-Ki4(scFv) R201K (n=6) every day for 5 days, afterwards in 2-days intervals. Treatment response with Gb-Ki4(scFv) R201K was compared to the unspecific Gb-H22(scFv) R201K control group using one-tailed t-test (GraphPad Prism, Version 4.0c). $p<0.05$ was considered to be statistically significant.

FIG. 18 shows the results of mouse experiments: Tumor reduction after treatment with cytolytic fusion protein: black triangles: Gb-Ki4(scFv) R201K, grey triangles Gb-Ki4 (scFv), grey squares Gb-H22(scFv) R201K. Y axis shows tumor size in %, X axis shows duration of experiment in days. A) Result for Kat2 transfected L428 tumors (fluorescent): 50 μg protein was injected intravenously daily for 5 days, starting one day after injection of cells. The tumor growth was calculated with the Cri Maestro System every day during treatment cycle. The tumor size on day 1 was set to 100%. The decelerated tumor growth of the group treated with the mutant compared to the unspecific control was confirmed statistically significant (*$p<0.001$). The difference between treatment with mutant and wildtype was statistically different with $p<0.05$ () except for day 2. B) Result for L540cy tumors: 50 μg protein was injected intravenously daily 5 for days, then in 2-days intervals until day 13 of the experiment. The tumor growth was measured via caliper in triplets. The difference between the curves was determined to be statistically significant ($p<0.05$). These results indicate that cytolytic fusion proteins based on the Granzyme B mutant R201K kills PI9 positive tumour cells in vivo whereby wildtype version does not lead to a decrease in tumor growth. Also on the PI9 negative cells L540cy, the mutant is functional and kills those cells in vivo as well.

In summary, the present disclosure pertains In advantageous embodiments to polypeptides comprising a serine protease variant of wild type human granzyme B as shown in SEQ ID NO: 1, having a modification at one or more positions selected from the group of positions that correspond structurally or by amino acid sequence homology to the positions 28 and/or 201, or variants, modified forms, homologs, fusion proteins, functional equivalents or functional fragments thereof, wherein said polypeptide having a greater apoptotic activity compared to wild type granzyme B.

The polypeptides of the present disclosure have one or more of the following characteristics:

- The functional fragment has at least 85%, at least 90%, at least 95 or at least 99% identity to amino acids 28-202 of SEQ ID NO: 1.
- The modification is a substitution, insertion, deletion, phosphorylation, acetylation like palmitoylation, methylation, sulphation, glycosylation, lipidation like isoprenylation, farnesylation, attachment of a fatty acid moiety, glypiation and ubiquitinylation, and/or
- The modification is at position 28 and/or 201, and/or
- The modification is a substitution.
- The modification is a conservative substitution.
- The modification is a neutral substitution.
- The modification is at least a substitution at position 28 and/or 201.
- The substitution is selected from the group consisting of R28A, R28E, R28K, R201A, R201E and R201K.
- The polypeptides comprise at least one of the substitutions R201A or R201K and/or R28K, or any combinations thereof.
- The polypeptide further comprises a substitution of one or more residues corresponding to position 35, 74 and/or 227.
- The substitution is selected from the group 35R, 74A and 227H, or any combinations thereof.
- The modified form of the polypeptide has at least a minimum percentage sequence identity and/or percent homology to polypeptide of claims 1 to 11, wherein the minimum percent identity and/or homology is at least 75%, at least 80%, at least 85%, at least 90%, at least 93%, at least 96%, at least 97%, at least 98% or at least 99%.

Furthermore, the present disclosure pertains in advantageous embodiments to nucleic acid molecules, selected from the group consisting of a) a nucleic acid molecule encoding a polypeptide according to the present disclosure;
b) a nucleic acid molecule encoding for a modified form of the polypeptide according to the present disclosure, preferably in which one or more amino acid residues are conservatively substituted;
c) a nucleic acid molecule that is a fraction, variant, homologue, derivative, or fragment of the nucleic acid molecule presented as SEQ ID NO:3, SEQ ID NO:4 or SEQ ID NO:5;
d) a nucleic acid molecule that is capable of hybridizing to any of the nucleic acid molecules of a)-c) under stringent conditions
e) a nucleic acid molecule that is capable of hybridizing to the complement of any of the nucleic acid molecules of a)-d) under stringent conditions
f) a nucleic acid molecule having a sequence identity of at least 95% with any of the nucleic acid molecules of a)-e) and encoding for a serine protease,
g) a nucleic acid molecule having a sequence identity of at least 70% with any of the nucleic acid molecules of a)-f) and encoding for a serine protease,
h) or a complement of any of the nucleic acid molecules of a)-g).

Furthermore, the present disclosure pertains in advantageous embodiments to vectors comprising a nucleic acid molecule according to the present disclosure and to host cells being transformed with a vector according to the present disclosure and/or comprising a nucleic acid molecule according to the present disclosure.

The present disclosure pertains in advantageous embodiments to isolated nucleic acid molecules selected from the group consisting of SEQ ID NO: 3, SEQ ID NO: 4 and SEQ ID NO: 5, and methods for preparing a polypeptide according to the present disclosure, which comprises culturing a host cell according to the present disclosure and isolating the polypeptide from the culture.

Further, the present disclosure pertains in advantageous embodiments to compositions comprising a polypeptide according to the present disclosure, wherein the compositions may be pharmaceutical, diagnostic or cosmetic compositions and uses of polypeptides according to the present disclosure for preventing or treating a disease like allergy, autoimmune reaction, tissue rejection reaction, or chronic inflammation reaction, and in particular cancer.

Furthermore, the present disclosure pertains in advantageous embodiments to purified complexes comprising a binding structure and a polypeptide according to the present disclosure, wherein a complex has one or more of the following characteristics:

The complex comprises a fusion protein including a binding structure and a polypeptide according to the present disclosure.

The binding structure belongs to the group of antigen binding polypeptides/proteins targeting cell type specific markers, in particular the binding structure is directed against cancer cell specific structures, disease specific structures of pathogenic substances or pathogenic matter.

The binding structure comprises moieties which are affinity moieties from affinity substances or affinity substances in their entirety selected from the group consisting of antibodies, antibody fragments, receptor ligands, enzyme substrates, lectins, cytokines, lymphokines, interleukins, angiogenic or virulence factors, allergens, peptidic allergens, recombinant allergens, allergen-idiotypical antibodies, autoimmune-provoking structures, tissue-rejection-inducing structures, immunoglobulin constant regions and their derivatives, mutants or combinations thereof.

The binding structure is an antibody or an antibody fragment selected from the group consisting of Fab, scFv; single domain, or a fragment thereof, bis scFv, $Fab_2$, $Fab_3$, minibody, diabody, maxibody, triabody, tetrabody and tandab, in particular the binding structure is a single-chain variable fragment (scFv), in particular specific for CD64 receptor and/or for CD30 receptor.

The purified complex according to according to the present disclosure further comprising at least one component S selected from the group consisting of an inducible promoter capable of regulating synthetic performance, a leader sequence capable of controlling protein biosynthesis, His tag, affinity tag, translocation domain amphiphatic sequence capable of translocating an apoptotic agent into a target cell, and a synthetic pro-granzyme B amphiphatic sequence capable of intracellular activation of a granzyme.

The component S is a leader sequence for secretory expression.

The component S is an enterokinase cleavage site enabling activation of the polypeptide according to the present disclosure.

The component S is an inducible promoter capable of regulating synthetic performance.

The component S is a HIS tag or affinity tag, enabling purification of the complex.

The complex comprises a single-chain variable fragment, a leader sequence for secretory expression, an enterokinase cleavage site, an inducible promoter, a HIS tag and a polypeptide according to the present disclosure.

Further, the present disclosure pertains in advantageous embodiments to:

Nucleic acid molecules coding for the complex according to according to the present disclosure.

Vectors carrying a nucleic acid molecule encoding a complex according to the present disclosure.

Cells transfected with the vector carrying a nucleic acid molecule encoding a complex according to the present disclosure.

Furthermore, the present disclosure pertains in advantageous embodiments to:

Medicaments comprising the complex according to the present disclosure in combination with a pharmacologically acceptable carrier or diluent.

Methods of treating a malignant disease, an allergy, autoimmune reaction, tissue rejection reaction, or chronic inflammation reaction comprising administering an effective amount of the complex according to the present disclosure to a patient in need thereof.

---

What is claimed is:

1. A polypeptide comprising a serine protease variant of the human granzyme B set forth by SEQ ID NO: 1, wherein said serine protease variant consists of SEQ ID NO: 1 with a substitution at the position $Arg^{201}$ of SEQ ID NO: 1, and wherein the serine protease variant has greater apoptotic activity and reduced sensitivity to the activity-inhibiting substance Serpin B9, as compared to the human granzyme B of SEQ ID NO: 1.

2. The polypeptide according to claim 1, wherein the serine protease variant is as set forth by SEQ ID NO: 9.

3. An isolated nucleic acid molecule encoding the polypeptide according to claim 1.

4. A composition comprising the polypeptide according to claim 1, wherein the composition is a pharmaceutical, diagnostic, or cosmetic composition.

5. A purified complex comprising a binding structure and a polypeptide according to claim 1.

6. The purified complex according to claim 5, wherein the complex further comprises a fusion protein, wherein the binding structure is an antigen binding polypeptide or protein that binds a cell type specific marker.

7. The purified complex according to claim 5, wherein the binding structure is an antibody or an antibody fragment selected from the group consisting of Fab, scFv; single domain, or a fragment thereof, bis scFv, $Fab_2$, $Fab_3$, minibody, diabody, triabody, tetrabody and tandab.

8. The polypeptide according to claim 1, wherein the serine protease variant differs from SEQ ID NO: 1 by a conservative mutation, wherein the conservative mutation is a substitution of the basic $Arg^{201}$ amino acid for another basic amino acid.

9. The polypeptide according to claim 1, wherein the amino acid sequence is SEQ ID NO: 8.

10. A vector comprising the nucleic acid molecule of claim 3.

11. A host cell transformed with the vector of claim 10.

12. A method for preparing the polypeptide of claim 1, which comprises culturing the host cell of claim 11 under conditions such that the host cell expresses the polypeptide encoded by the nucleic acid molecule and isolating the polypeptide from the culture.

* * * * *